(12) United States Patent
Putnam et al.

(10) Patent No.: US 7,790,113 B2
(45) Date of Patent: Sep. 7, 2010

(54) VISUAL, CONTINUOUS AND SIMULTANEOUS MEASUREMENT OF SOLUTION AMMONIA AND HYDROGEN ION CONCENTRATION

(75) Inventors: David L. Putnam, Sammamish, WA (US); Janice A. Sharick, Sammamish, WA (US); Jason A. Putnam, Sammamish, WA (US)

(73) Assignee: Photonic BioSystems, Inc., Sammamish, WA (US)

( * ) Notice: Subject to any disclaimer, the term of this patent is extended or adjusted under 35 U.S.C. 154(b) by 638 days.

(21) Appl. No.: 11/696,695

(22) Filed: Apr. 4, 2007

(65) Prior Publication Data

US 2008/0076184 A1 Mar. 27, 2008

Related U.S. Application Data

(60) Provisional application No. 60/788,983, filed on Apr. 4, 2006.

(51) Int. Cl.
*G01N 27/00* (2006.01)
(52) U.S. Cl. .................... 422/82.03; 422/82.01
(58) Field of Classification Search ............... 422/82.01, 422/82.03
See application file for complete search history.

(56) References Cited

U.S. PATENT DOCUMENTS

| | | | |
|---|---|---|---|
| 3,953,566 A | 4/1976 | Gore | |
| 3,998,591 A | 12/1976 | Eckfeldt | |
| 4,187,390 A | 2/1980 | Gore | |
| 4,201,548 A | 5/1980 | Tamaoku | |
| 4,513,087 A | 4/1985 | Giuliani | |
| 4,716,074 A | 12/1987 | Hurley | |

(Continued)

FOREIGN PATENT DOCUMENTS

EP          0169055          1/1986

(Continued)

OTHER PUBLICATIONS

Alabbas et al., "Design and Performance Features of an Optical-fibre Reflectance pH Sensor," Analytical Proceedings, Nov. 1989, pp. 373-375, vol. 26.

(Continued)

*Primary Examiner*—Edward M Johnson
(74) *Attorney, Agent, or Firm*—Barry L. Davison, J. D.; Davis Wright Tremaine LLP

(57) ABSTRACT

Particular aspects provide novel devices and methods for accurately measuring total ammonia ($NH_3$ plus $NH_4^+$) in a solution (e.g., freshwater and saltwater) by spatially proximate, simultaneous and continuous quantitative measurement of solution pH and ammonia. The devices overcome prior art inaccuracies relating to non-homogeneous sampling, and to spatial, temporal and thermal sampling discontinuities. Particular embodiments provide a combination pH and ammonia measuring device, comprising: a submersible member; a submersible non-bleeding ammonia-sensing portion attached to the submersible member and suitable to provide for a continuous visual indicator of solution ammonia concentration; a submersible non-bleeding pH-sensing portion attached to the submersible member and suitable to provide for a continuous visual indicator of solution pH; visual ammonia and pH indicator comparison means suitable for comparative quantitative determination of solution ammonia concentration and pH. Additional aspects provide novel ultra-sensitive devices and methods using same for measuring ammonia in air or solution.

50 Claims, 2 Drawing Sheets

U.S. PATENT DOCUMENTS

| | | | |
|---|---|---|---|
| 4,830,010 | A | 5/1989 | Marshall |
| 4,947,861 | A | 8/1990 | Hamilton |
| 5,013,668 | A | 5/1991 | Fields |
| 5,308,771 | A | 5/1994 | Zhou |
| 5,315,673 | A | 5/1994 | Stetter |
| 5,322,797 | A | 6/1994 | Mallow |
| 5,366,631 | A | 11/1994 | Adiletta |
| 5,415,838 | A | 5/1995 | Rieger |
| 5,494,640 | A | 2/1996 | Simon |
| 5,543,621 | A | 8/1996 | Sauke |
| 5,753,285 | A | 5/1998 | Horan |
| 5,763,360 | A | 6/1998 | Gundel |
| 5,848,975 | A | 12/1998 | Phillips |
| 5,952,237 | A | 9/1999 | Tanaka |
| 6,051,437 | A | 4/2000 | Luo |
| 6,067,989 | A | 5/2000 | Katzman |
| 6,107,099 | A | 8/2000 | Munkholm |
| 6,149,952 | A | 11/2000 | Horan |
| 6,328,932 | B1 | 12/2001 | Carter |
| 6,670,617 | B2 | 12/2003 | Banks |
| 7,033,839 | B1 | 4/2006 | Dobler |
| 2003/0003589 | A1 | 1/2003 | Khalil |
| 2008/0041136 | A1 | 2/2008 | Kopelman |

FOREIGN PATENT DOCUMENTS

| | | |
|---|---|---|
| EP | 0928966 | 7/1999 |
| JP | 57-93253 | 6/1982 |
| JP | 61-218941 | 9/1986 |
| JP | 3-255943 | 11/1991 |
| JP | 5-107240 | 4/1993 |
| WO | WO 98/22813 | 5/1998 |

OTHER PUBLICATIONS

Andres et al., "Fibre-optic reflectometric study on acid-base equilibria of immobilized indicators: effect of the nature of immobilizing agents," Analytica Chimica Acta, 1991, pp. 165-168, vol. 251.

Bacci et al., "Spectrophotometric Investigations on Immobilezed Acid-Base Indicators," Analytica Chimica Acta, Apr. 15, 1988, pp. 343-348, vol. 207.

Baron et al., "Hydrophobic membrane sensors for the optical determination of hydrogen chloride gas," Sensors and Actuators B: Chemical, 1996, pp. 511-515, vol. 34.

Beswick et al., "Optical Detection of Toxic Gases Using Fluorescent Porphyrin Langmuir-Blodgett Films," Journal of Colloid and Interface Science, Jul. 1988, pp. 146-155, vol. 124.

Bogomolov et al., Avtomatizatsiya Khimicheskikh Proizvodstv, 1968, pp. 66-73.

Bondarenko et al., Khimicheskaya Fizika, 1994, pp. 116-119, vol. 13.

Callahan et al., "Investigation of Relative Humidity Effects on the Response Behavior of a pH Indicator-Based OWG Vapor Sensor," Talanta, 1993, pp. 431-444, vol. 40.

Cui et al., "Optical fibre PH sensor based on immobilised Indicator," Society of Photo-Optical Instrumentation Engineers, 1991, pp. 386-391, vol. 1572.

Fan et al., "Research on multi-parameter environmental sensing technique based on optical fiber," Huanjing Kexue Xuebao, 1999, pp. 200-204, vol. 19.

Gisclard et al., "A Simple Device for Air Analysis," American Industrial Hygiene Association Quarterly, 1953, pp. 23-25, vol. 14.

Giuliani et al., "Reversible optical waveguide sensor for ammonia vapors," Optics Letters, 1983, pp. 54-56, vol. 8.

Golubkov et al., "Application of pH dyes for ammonia sensing by portable analyzer," SPIE, 1992, pp. 227-232, vol. 1637.

Graham et al., "Campylobacter Pylori Detected Noninvasively by the 13C-Urea Breath Test," Lancet, May 23, 1987, pp. 1174-1177, vol. 1.

Hauser et al., "All Solid-State Instrument for Absorbance Based Optical Gas Sensor Membranes," Instrumentation Science & Technology, 1997, pp. 147-156, vol. 25.

Ito et al., "Hyperammonaemia and Helicobacter pylori," Lancet, Jul. 8, 1995, pp. 124-125, vol. 346.

Jicong et al., "15NH4+ Excretion Test: a New Method for Detection of Helicobacter pylori Infection," Journal of Clinical Microbiology, Jan. 1992, pp. 181-184, vol. 30.

Kirkbright et al., "Fibre-optic pH Probe Based on the Use of an Immobilised Colorimetric Indicator," Analyst, Aug. 1984, pp. 1025-1028, vol. 109.

Kirkbright et al., "Studies with Immobilised Chemical Reagents Using a Flow-cell for the Development of Chemically Sensitive Fibre-optic Devices," Analyst, 1984, pp. 15-17, vol. 109.

Klein et al., "Integrated-optic ammonia sensor," Fresenius' Journal of Analytical Chemistry, 1994, pp. 394-398, vol. 349.

Kvasnik et al., "Distributed chemical sensing utilising evanescent wave interations," SPIE, 1983, pp. 75-82, vol. 1172.

Lipski et al., "Blood ammonia and Helicobacter pylori," Australian & New Zealand Journal of Medicine, Jun. 1992, p. 311, vol. 22.

Maher et al., "A Fiber Optic Chemical Sensor for Measurement of Groundwater pH," Journal of Testing and Evaluation, 1993, pp. 448-452, vol. 21.

Malins et al., "Fibre optic ammonia sensing employing novel near infrared dyes," Sensors and Actuators B: Chemical, 1998, pp. 359-367, vol. 51.

Marshall et al., "A 20-Minute Breath Test for Helicobacter pylori," American Journal of Gastroenterology, Apr. 1991, pp. 438-445, vol. 86.

Meredith et al., "Total Ammonia Monitoring Using an Optrode and an Electrochemical Sample pH Adjusting System," Water Science and Technology, 1998, pp. 301-307, vol. 37.

Millipore, Fluoropore Membrane Filter, Product Family Information, retrieved from http://www.millipore.com/catalogue/item/FHUP04700 (2 pages).

Millipore, Millipore Technical Publications, PTFE Membrane Filters, retrieved from http://www.millipore.com/techpublications/tech1/pf1044en00 (2 pages).

Millipore, Data Sheet, PTFE Membrane Filters, retrieved from http://millipore.com/publications.nsf/a73664f9f981af8c852569b9005b4eee/eb3322447c18c72d85256a6900681859/$FILE/ATTZVFBV/PTFE%20data%20sheet%20PF1044EN00.pdf (4 pages).

Mills et al., "Plastic Colorimetric Film Sensors for Gaseous Ammonia," Mikrochimca Acta, 1995, pp. 225-236, vol. 121.

Mohr et al., "Application of Chromogenic and Fluorogenic Reactands in the Optical Sensing of Dissolved Aliphatic Amines," Analytical Chemistry, 1998, pp. 3868-3873, vol. 70.

Mohr et al., "Synethsis and characterization of fluorophore-absorber pairs for sensing of ammonia based on fluorescence," Analytica Chimica Acta, 1998, pp. 119-128, vol. 360.

Mokuolu et al., "Gastric Juice Urease Activity as a Diagnostic Test for Helicobacter pylori Infection," American Journal of Gastroenterology, Apr. 1997, pp. 644-648, vol. 92.

Morales-Bahnik et al., "An optochemical ammonia sensor based on immobilized metalloporphyrins," Chemical Abstracts, 1994, vol. 121, abstract 41603j.

Morales-Bahnik et al., "An optochemical ammonia sensor based on immobilized metalloporphyrins," Sensors and Actuators, 1994, p. 493-496, vol. 121.

Moreno et al., "Analytical performance of an optical pH sensor for acid-base titration," Analytica Chimica Acta, 1990, pp. 35-40, vol. 230.

Nevzorov et al., "Physiochemical processes in a fiber-optical ammonia," Khimicheskaya Fizika, 1994, pp. 108-115, vol. 13.

NIH Consensus Conference (NIH Consensus Development Panel on Helicobacter pylori in Peptic Ulcer Disease), "Helicobacter pylori in Peptic Ulcer Disease," JAMA, Jul. 6, 1994, pp. 65-69, vol. 272.

Noreña-Franco et al., "Chemically sensitive films fo rthe detection of hazardous substances employing cyanine and nitroso near infrared dyes," The Analyst, 1998, pp. 2185-2189, vol. 123.

Novikov et al., "Glassy spectral gas sensors based on the immobilized indicators," SPIE, 1995, pp. 119-129, vol. 2550.

Opilski et al., "Spectral properties of bromophenol blue used as sensor layer of ammonia vapours," SPIE, 1999, pp. 172-178, vol. 3731.

Plevris et al., "Hyperammonaemia in cirrhosis and Helicobacter pylori infection," Lancet, Oct. 21, 1995, p. 1104, vol. 346, No. 8982.

Potyrailo et al., "Fiber optic and portable instruments for ammonia sensing in the field operating conditions," SPIE, 1993, pp. 76-84, vol. 2069.

Potyrailo et al., "Fiber-Optic Sensor for Ammonia Vapors of Variable Temperature," SPIE, Aug. 1991, pp. 434-438, vol. 1572 (International Conference on Optical Fibre Sensors in China OFS(C) '91, Culshaw and Liao, editors).

Potyrailo et al., "pH Indicator Based Ammonia Gas Sensor: Studies of Spectral Performance Under Variable Conditions of Temperature and Humidity," Analyst, Mar. 1994, pp. 443-448, vol. 119.

Product Description: AEM 5700 Antimicrobial Solution, Aegis Environments, Inc., Midland, Texas, retrieved from http:www.aegisasia.com/antimicrobial.html on Feb. 6, 2009 (5 pages).

Product Description: Cyclopore Polycarbonate and Polyester Membranes, Whatman, Inc. (now GE Healthcare), Florham Park, New Jersey, retrieved from http://www.whatman.com/products.aspx?PID=19 on Feb. 6 2009 (4 pages).

Product Description: Furon, Hoosick Falls, New York, retrieved from http://www.chrtape.com/Data/Element/Node/Application/application_edit.asp?ele_ch_id=A0000000000000002296 on Feb. 6, 2009 (2 pages).

Product Description: Millex-GP Filter Devices, Millipore Corp., Billerica, Massachusetts, retrieved fromhttp://www.millipore.com/msds.nsf/a73664f9f981af8c852569b9005b4eee/85256f0a005296f28525694b003beb81/$FILE/M102086.pdf retrieved Feb. 6, 2009 on Feb. 6, 2009 (4 pages).

Product Description: Porous PTFE Film (now Gore Medical Membranes), Gore-Tex, Elkton, Maryland (now W.L. Gore & Associates, Inc., Newark, Delaware), retrieved from http://www.gore.com/en_xx/products/filtration/micro/gore_microfiltration_media.html (1 page), http://www.gore.com/en_xx/products/medical/index.html (1 page), and http://www.gore.com/en_xx/products/medical/oem/membranes/index.html (1 page) on Feb. 26, 2009.

Product Description: PTFE Thread Seal Tapes, Plastomer Technologies, Houston, Texas, retrieved from http://www.plastomertech.com/ptfethreadsealtape.htm on Feb. 6, 2009 (2 pages).

Product Description: Sterivex-GP Filter Devices, Millipore Corp., Billerica, Massachusetts, retrieved fromhttp://www.millipore.com/msds.nsf/a73664f9f981af8c852569b9005b4eee/85256f0a005296f285256d5e0041070f/$FILE/M113264.pdf retrieved Feb. 6, 2009 on Feb. 6, 2009 (4 pages).

Product Description: Supor 100, Pall Corporation, East Hills, New York, retrieved from http://labfilters.pall.com/catalog/924_20070.asp on Feb. 6, 2009 (6 pages).

Product Description: Teflon Tape (now Taega Tape), St. Gobain Performance Plastics Corporation, Hoosick Falls, New York (now Taega Technologies, Inc., Kernersville, North Carolina), retrieved from http://www.taegatech.com (1 page), http://www.taegatech.com/images/sizemainlarge.jpg (1 page), and http:www.taegatech.com/techdata.htm (1 page) on Feb. 26, 2009.

Product Description: Zefluor, Pall Corporation, East Hills, New York, retrieved from http://labfilters.pall.com/catalog/924_20061.asp on Feb. 6, 2009 (1 page).

Product Description: Zylon, Pall Corporation, East Hills, New York, retrieved from http://labfilters.pall.com/catalog/924_20061.asp on Feb. 6, 2009 (1 page).

Sadaoka et al., :Optical Properties of Cresyl Violet-Polymer Composites for Quantification of Humidity and Ammonia Gas in Ambient Air, Journal of Materials Chemistry, 1993, pp. 247-251, vol. 3, No. 3.

Sellien et al., "Development of an optical-chemical sensor for the detection of ammonium ions," Analytica ChimicaActa, 1992, pp. 83-88, vol. 269.

Spear et al., "Ammonia Measurements in Mammalian Cell Culture Media with a Diffuse Reflectance-Based Fiberoptic Ammonia Sensor," Applied Biochemistry and Biotechnology, 1998, pp. 175-186, vol. 75.

Test Description (Ammonia): Aquarium Pharmaceuticals, Inc., Chalfont, Pennsylvania, Ammonia $NH_3/NH_4^=$ Test Kit, retrieved from http://aquariumpharm.com/Products/Product.aspx?ProductID=69 on Jun. 2, 2008 (1 page).

Test Description (Ammonia): Jungle Laboratories Corporation, Cibolo, Texas (now Spectrum Brands, Inc., Atlanta, Georgia), Ammonia Quick Dips® Test Strips, retrieved from http://www.junglelabs.com/pages/details.asp?item=TK300 on Jun. 2, 2008 (1 page).

Test Description (Ammonia): LiveMeter Technologies, Inc. (now AquaStasis Corporation, Seattle, Washington), $LiveNH_3$, retrieved from http://www.aquastasis.com/products.html on Jun. 3, 2008 (1 page).

Test Description (Ammonia): Mardel (now AquaStasis Corporation, Seattle, Washington), Ammonia Test Strips, retrieved from http://www.petsmart.com/product/index.jsp?productId=2753385 on Jun. 2, 2008 (1 page).

Test Description (Ammonia): Seachem, Madison, Georgia, Ammonia Alert™, retrieved from http://www.seachem.com/products/product_pages/AmmoniaAlert.html on Jun. 3, 2008 (1 page).

Test Description (Helicobacter Pylori): Tri-Med Specialties Inc., a division of Ballard Medical, Draper, Utah (now Kimberly-Clark Corporation), PYtest (Carbon 14 Urea Breath Test), retrieved from http://www.breathtest.com/html/three_easy_steps.htm (2 pages) and http://www.breathtest.com/html/global.htm in 2002 (1 page); and CLOtest (Campylobacter Like Organism Test), retrieved from http://www.breathtest.com/html/clotest.htm in 2002 (3 pages).

Test Description (pH): Aquarium Pharmaceuticals, Inc., Chalfont, Pennsylvania, pH Test & Adjuster Kit, retrieved from http://aquariumphar.com/Products/Productaspx?ProductID=73 on Jun. 5, 2008 (1 page).

Test Description (pH): EMD Chemicals, Inc., Gibbstown, New Jersey, ColorpHast® Test Strips, retrieved from http://www.emdchemicals.com/analytics/literature/displaylit.asp?location=ar&litfile=EnvTst_colorpHast.html on Jun. 3, 2008 (2 pages).

Test Description (pH): Jungle Laboratories Corporation, Cibolo, Texas (now Spectrum Brands, Inc., Atlanta, Georgia), pH Level Quick Dig® Test Strips, retrieved from http://www.junglelabs.com/pages/details.asp?item=TK100 retrieved Jun. 5, 2008 (1 page).

Test Description (pH): LiveMeter Technologies, Inc. (now AquaStasis Corporation, Seattle, Washington), LivepH, retrieved from http://www.aquastasis.com/products.html on Jun. 3, 2008 (1 page).

Test Description (pH): pH-ion Nutrition, Scottsdale, Arizona, pHion pH Stix™, retrieved from http://www.ph-ion.com/index.asp?PageAction=VIEWCATS&Category=205 on Jan. 27, 2009 (5 pages).

Thijs et al., "Diagnostic Tests for Helicobacter pylori: A Prospective Evaluation of Their Accuracy, without Selecting a Single Test as the Gold Standard," American Journal of Gastroenterology, Oct. 1996, pp. 2125-2129, vol. 91, No. 10.

Veldhuyzen Van Zanten et al., "14C-Urea Breath Test for the Detection of Helicobacter pylori," American Journal of Gastroenterology, Apr. 1990, pp. 399-403, vol. 85, No. 4.

Wyatt et al., "Characterization and Comparison of Three Fibre-Optic Sensors for Iodide Determination Based on Dynamic Fluorescence Quenching of Rhodamine 6G," Analytical Chemistry, Sep. 15, 1987, pp. 2272-2276, vol. 59, No. 18.

Zhou et al., "Porous plastic optical fiber sensor for ammonia measurement," Applied Optics, Jun. 1, 1989, pp. 2022-2025, vol. 28, No. 11.

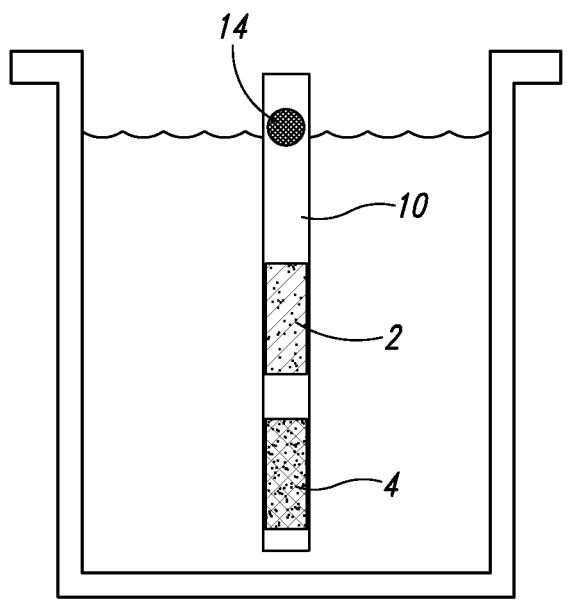
Fig. 2
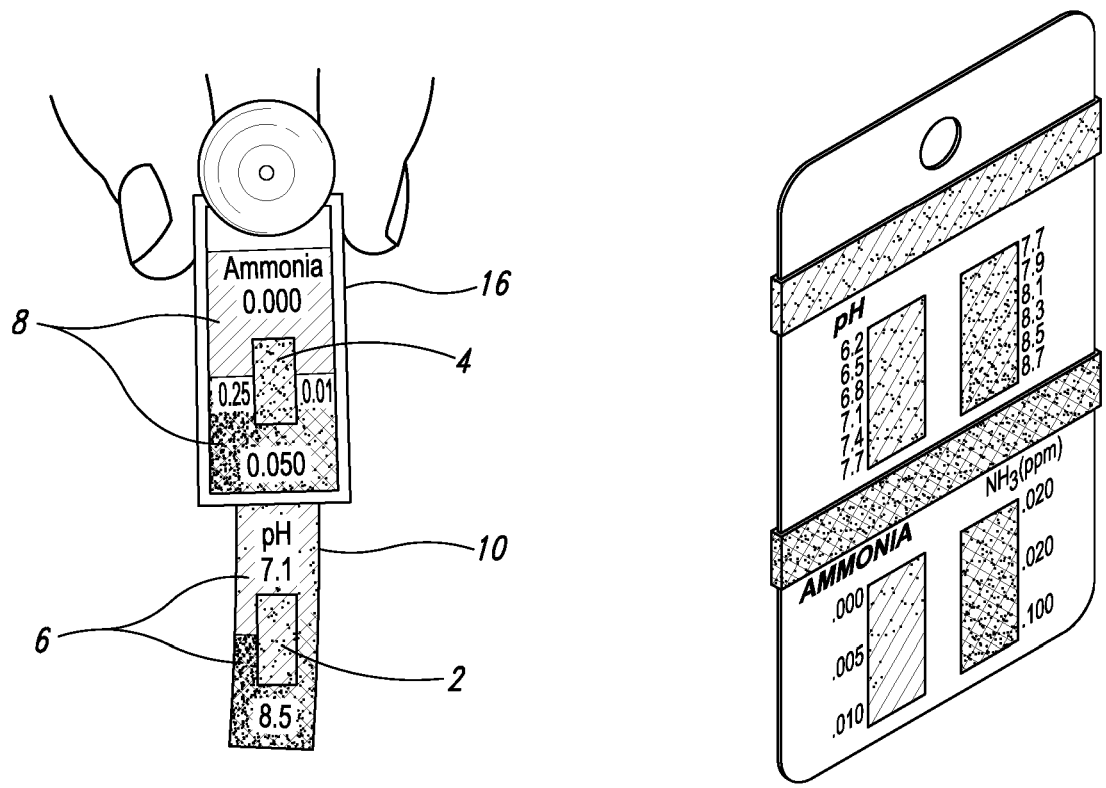
Fig. 3
Fig. 4

VISUAL, CONTINUOUS AND SIMULTANEOUS MEASUREMENT OF SOLUTION AMMONIA AND HYDROGEN ION CONCENTRATION

FIELD OF THE INVENTION

Aspects of the present invention relate generally to means for measuring the status of an air or aqueous environment (e.g., freshwater and saltwater), and more particularly to novel methods and devices for accurately measuring total ammonia ($NH_3$ plus $NH_4^+$) in a solution by proximate, simultaneous and continuous quantitative measurement of solution pH and ammonia, and to novel methods and devices for measuring ammonia in air or in solution.

BACKGROUND

Two forms of ammonia are present in any aqueous environment (e.g., aquarium, pool, hot tub, lake, river, pond, manufacturing container, etc.). Ammonia ($NH_3$), sometimes referred to as 'toxic ammonia,' is normally present in lower concentrations than ammonium ion ($NH_4^+$), which is considered to be less toxic. 'Total ammonia' refers to the sum of ammonia plus ammonium ion levels in a solution.

It is important to know the ammonia concentration in a solution, particularly in an environment where organisms are present, due to its toxicity. Most current visual tests, however, are only capable of measuring 'total ammonia' ($NH_3$ plus $NH_4^+$). These provide an indirect measure of the ammonia ($NH_3$) concentration, and are therefore at least relevant in estimating, for example, toxic ammonia ($NH_3$) levels in an aqueous system (e.g., aquarium, pool, hot tub, lake, river, pond, manufacturing container, etc.).

The relative levels of the two forms of ammonia ($NH_3$ and $NH_4^+$) change, equilibrating between forms, with changes in pH and temperature. The pH effect on the equilibrium between ammonia and ammonium concentration, described by a derivation of the Henderson-Hasselbach equation, is a exponential function:

$$[NH3] = \frac{[NH4]}{10^{(ph-pKa)}}$$

Consequently, small changes in the pH result in large changes in the equilibrium balance of the two forms of ammonia. Similarly, temperature effects on the $NH_3$:NH4 equilibrium constant (pKa) which in turn affects interpretation of the Henderson-Hasselbach relationship and prediction of the solution concentration of $NH_3$. Ultimately, the amount of ammonia rises with increases in pH and solution temperature. Sampling variation arising as a result of variation in the temperature, time, and sampling position/location within a given aqueous environment will therefore make interpretation of the Henderson-Hasselbach relationship incorrect. Therefore, in addition to knowing the ammonia content, it is important to know the ammonium ($NH_4^+$) and/or total ammonia ($NH_3$ plus $NH_4^+$) level to understand potential toxic risk in an aquatic system. In conditions involving high ammonium content and low pH, a rise in pH would result in a subsequent large equilibration shift of $NH_4^+$ into a high level of toxic $NH_3$, quickly creating a hazardous situation.

In theory, if the concentration of either the ammonia, or the ammonium, or the total ammonia is determined through testing, in conjunction with the pH of a solution, and the temperature is known, then based on the equilibrium relationship, the concentration of the other parameters can be established. In practice, since both the nitrogenous products in water (e.g., ammonia), temperature and pH levels can constantly vary, and in view of inherent limitations of existing test methods, the measurement and tracking over time of these fluctuating parameters is problematic, particularly with the simple procedures and kits typically used.

Current visual tests for 'total ammonia' and pH rely almost exclusively on single-point measurements, typically performed with an extricated discrete sample of the solution to be tested. Additionally, most require addition of reagents that engender non-reversible chemical reactions. Alternatively, there are single-use devices that can be immersed briefly in a solution to be tested, without removing a test aliquot, but contain reagents that are soluble, and that leach, bleed or diffuse from the sensing device. Such devices are only used for instantaneous measurements, at one time point, and are not designed for reversibility or stability with prolonged immersion. Prior art examples of such single-point pH test kits include: a freshwater only pH test kit requiring a sample aliquot of freshwater and using a liquid reagent (Aquarium Pharmaceuticals, Inc.), where the product is only useful for freshwater because its range is too narrow to be applicable to saltwater, which typically has higher pH levels; and a pH dip test using a test strip with an indicator reagent pad (Quick Dip™ pH test; Jungle Laboratories Corporation); and a pH dip test using non-bleeding single-test indicator strips (e.g., COLORPHAST® pH 6.5-10.0; made by EMD Chemicals, Inc. Gibbstown, N.J., USA). Additionally, there is one 'in-tank' pH sensor that is a continuous in-tank freshwater only pH sensor (LivepH™ from LiveMeter™ Technologies, Inc.).

Prior art examples of such single point ammonia test kits include: a total ammonia freshwater-only test kit requiring a sample aliquot of freshwater, and using a liquid reagent (Aquarium Pharmaceuticals, Inc.); and a total ammonia test using a test strip with an indicator reagent pad (Ammonia Test Strips, from Mardel). Additionally, one visual test for directly measuring, at least qualitatively, only the toxic ammonia ($NH_3$) has also been developed, which is a continuous in-tank ammonia ($NH_3$) sensor (Ammonia Alert™, from Seachem).

Therefore, on the one hand, a total ammonia value obtained using a 'total ammonia' single-point test kit, is somewhat useful in monitoring for potentially toxic conditions. However, depending on parameters such as pH, temperature and spatial positioning where the point measurement is made within an aqueous environment, such total ammonia measurements can be indefinite and/or misleading, with respect to what the actual toxic ammonia level is. On the other hand, prior art determinations of total ammonia, based on independent separate determinations of pH and ammonia, are inherently inaccurate because of thermal, temporal and spatial inhomogeneity; for example, where multiple independent test samples are withdrawn for either pH or ammonia (or for either pH and total ammonia) for testing at differing times from a larger aqueous environment. Additionally, the 'read-out' of prior art ammonia measurement devices (the AMMONIA ALERT™ card of SEACHEM™) is qualitative (e.g., safe, dangerous, toxic) and not quantitative, precluding accurate determinations of ammonia ($NH_3$) concentration.

Therefore, prior art methods and devices for measuring 'total ammonia' do not provide for accurate determination of ammonia, and independent prior art determinations of pH and ammonia have not afforded accurate quantitative determination of either ammonia or total ammonia ($NH_3$ plus $NH_4^+$).

Therefore, there is a pronounced need in the art for novel and cost-effective methods and devices for accurately determining pH, ammonia ($NH_3$) and total ammonia ($NH_3$ plus $NH_4^+$) in an aqueous environment, and which overcome prior art inaccuracies relating to non-homogeneous sampling, and to spatial, temporal and thermal sampling discontinuities. There is a pronounced need in the art for novel and cost-effective methods and devices for accurate quantitative and continuous determination of pH, ammonia ($NH_3$) and total ammonia ($NH_3$ plus $NH_4^+$) in an aqueous environment.

There is, in view of its potential toxicity, also a pronounced need in the art for more sensitive devices and methods to quantitatively measure ammonia to provide for earlier detection of potential problems in both solution (e.g., aqueous) and air environments.

SUMMARY OF THE INVENTION

Particular aspects provide novel methods and devices for accurately measuring total ammonia ($NH_3$ plus $NH_4^+$) in a solution by proximate, simultaneous and continuous quantitative measurement of solution pH and ammonia. The inventive proximate, simultaneous and continuous solution measurement devices are unique, and overcome inaccuracies of the prior art relating to non-homogeneous sampling, and to spatial, temporal and thermal sampling discontinuities that give rise to inaccurate ammonia, and total ammonia determinations.

Additional aspects provide novel ultra-sensitive ammonia detection devices and methods for using same.

Particular embodiments provide a combination pH and ammonia measuring device for simultaneous, continuous measurement of solution pH and ammonia, comprising: a submersible member, suitable to be at least partially submersible in a solution; a submersible ammonia-sensing portion attached to the submersible member, the ammonia-sensing portion having non-dissociating detection means suitable to provide for a continuous visual indicator of solution ammonia concentration; a submersible pH-sensing portion attached to the submersible member, the pH-sensing portion having non-dissociating detection means suitable to provide for a continuous visual indicator of solution pH; a visual ammonia indicator comparison means, comparable with the continuous visual indicator of the ammonia-sensing portion for standardized quantitative determination of solution ammonia concentration; and a visual pH indicator comparison means, comparable with the continuous visual indicator of the pH-sensing portion for standardized quantitative determination of solution pH.

Additional embodiments provide a combination pH and ammonia measuring device for simultaneous, continuous measurement of solution pH and ammonia, comprising: an attachment base member; a submersible member, reversibly attachable to the attachment base member, and suitable to be at least partially submersible in a solution; a submersible ammonia-sensing portion attached to the submersible member, the ammonia-sensing portion having non-dissociating detection means suitable to provide for a continuous visual indicator of solution ammonia concentration; a submersible pH-sensing portion attached to the submersible member, the pH-sensing portion having non-dissociating detection means suitable to provide for a continuous visual indicator of solution pH; a visual ammonia indicator comparison means, comparable with the continuous visual indicator of the ammonia-sensing portion for standardized quantitative determination of solution ammonia concentration; and a visual pH indicator comparison means, comparable with the continuous visual indicator of the pH-sensing portion for standardized quantitative determination of solution pH.

Yet further embodiments provide a method determining the total ammonia concentration in a solution, comprising: submersing, in a solution, a combination pH and ammonia measuring device for simultaneous, continuous measurement of solution pH and ammonia; and determining the total ammonia ($NH_3$ plus $NH_4^+$), based on a visual indicator of solution ammonia concentration and a visual indicator of solution pH. Preferably, the combination pH and ammonia measuring device for simultaneous, continuous measurement of solution pH and ammonia are as disclosed herein.

Yet further embodiments provide an ammonia detection device, comprising porous matrix polytetrafluoroethylene (PTFE) having an ammonia-sensitive immobilized dye, the immobilized dye suitable to provide for a calorimetric determination of ammonia level, and wherein the detectible range of ammonia comprises a range of about 0.005 to about 0.1 ppm. Preferably, the ammonia-sensitive immobilized dye is BPB dye. Preferably, the porous matrix polytetrafluoroethylene (PTFE) comprises a composite supported microporous PTFE medium, comprising a PTFE microporous membrane having secured directly to at least one face thereof a PTFE web of microfibres.

Additional embodiments provide a method for detecting ammonia in air, comprising exposing the above-described ammonia detection device to air, wherein a calorimetric determination of air ammonia level is, at least in part, afforded. Particular aspects of this method comprise optical sensing to interrogate the color of the ammonia-sensitive immobilized dye.

Further embodiments provide a method for detecting ammonia in solution, comprising exposing the above-described ammonia detection device to a test solution, wherein a calorimetric determination of solution ammonia level is, at least in part, afforded. Particular aspects of this method comprise optical sensing to interrogate the color of the ammonia-sensitive immobilized dye.

Yet further methods comprise enhanced sensitivity sensors, comprising porous matrix polytetrafluoroethylene (PTFE) having one or more immobilized indicator dyes to provide for an enhanced calorimetric determination of detected substance. In particular aspects, the porous matrix polytetrafluoroethylene (PTFE) comprises a composite supported microporous PTFE medium, comprising a PTFE microporous membrane having secured directly to at least one face thereof a PTFE web of microfibres.

BRIEF DESCRIPTION OF THE DRAWINGS

FIGS. 1A-1D show a combination sensor strip as a standalone sensor strip (FIGS. 1A and 1D, in gray-scale and color, respectively), and as reversibly attached to a sensor card having integral color charts (FIGS. 1B and 1C, in gray-scale and color, respectively).

FIG. 2 shows, according to particular aspects of the present invention, the exemplary combination pH and ammonia measuring device embodiment of FIG. 1D (standalone sensor strip, the being used to continuously measure pH and ammonia in an aqueous environment (e.g., aquarium, pool, hot tub, lake, river, pond, manufacturing container, etc.).

FIG. 3 shows, according to further aspects of the present invention, another exemplary combination pH and ammonia measuring device embodiment.

FIG. 4 shows, according to yet further aspects of the present invention, another exemplary combination pH and ammonia measuring device embodiment.

DETAILED DESCRIPTION OF THE INVENTION

Definitions

Figure 1:
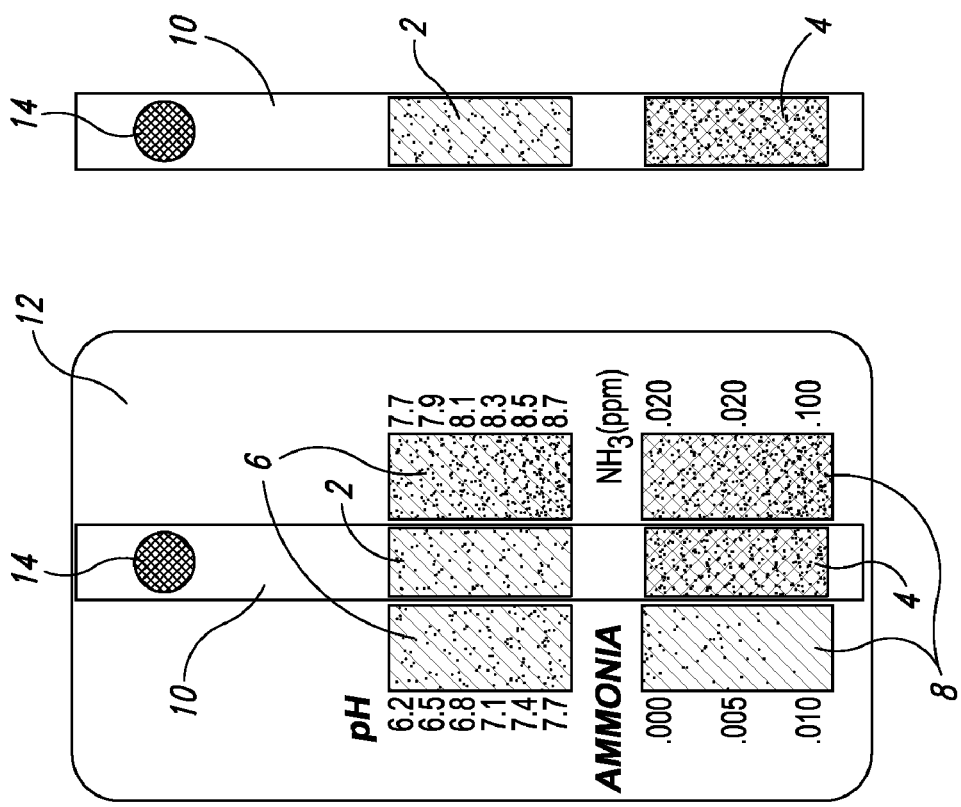
FIGS. 1A-D show exemplary embodiments of a combination pH and ammonia measuring device according to particular aspects of the present invention.

With respect to proximate, simultaneous, continuous measurement of solution pH and ammonia using the at least one pH-sensing and the at least one ammonia-sensing portions of the present inventive devices, the term "proximate" refers to the fact that the at least one ammonia-sensing portion, and the at least one pH-sensing portion are: (i) relatively disposed in a close, near, adjacent or adjoining spatial relationship to one another, but not necessarily contiguous; and (ii) are integral with or attached to a submersible member, or a plurality of proximately connected, coordinately-submersible members, such that sensors are coordinately and proximately submersible in the solution to be tested. Accordingly, with respect to the submersible member, or the plurality of proximately connected, coordinately-submersible members, the term "submersible" refers to the fact the member or proximate members must be at least partially submersible in a solution; that is, must be sufficiently submersible to enable coordinate, proximate submersion of the integral or attached sensing portions.

With respect to proximate, simultaneous, continuous measurement of solution pH and ammonia using the at least one pH-sensing and the at least one ammonia-sensing portions of the present inventive devices, the term "simultaneous," as used herein refers to concurrent or coincident in real-time measurement of pH and ammonia by the proximate, coordinately submersed pH-sensing and ammonia-sensing portions. Therefore, while pH and ammonia are measured using separate but proximate sensing portions, the sensing of pH and ammonia is concurrent or coincident in real-time as enabled by the instant inventive devices. Significantly, the instant proximate, simultaneous and continuous solution measurement devices are unique, and overcome inaccuracies of the prior art relating to non-homogeneous sequential sampling, and to spatial, temporal and thermal sampling discontinuities that give rise to inaccurate total ammonia determinations.

With respect to proximate, simultaneous, continuous measurement of solution pH and ammonia using the at least one pH-sensing and the at least one ammonia-sensing portions of the present inventive devices, the term "continuous" refers to the fact that, in each case, the at least one ammonia-sensing portion, and the at least one pH-sensing portion are: (i) sufficiently stable to be submersed within the solution being tested over an extended time (e.g., minutes, hours, days, weeks, months, years; preferably, weeks, months or years; most preferably months or years) without substantial deterioration (e.g., bleeding, break-down, etc.) of the indicator means (e.g., visual indicator means); and (ii) the detection means is 'reversible' in the sense that the pH and ammonia detection means is in sufficient equilibrium with the test solution so as to continuously track or reflect changes (e.g., real-time changes) in pH and ammonia, respectively, as the pH and ammonia values vary (e.g., reversibly increasing or decreasing) within the detectable range of the respective sensors.

As described in relation to continuous measurement, "stable detection means," as used herein refers to the fact that, in each case, the pH and ammonia-sensing portions are sufficiently stable so as to be submersible within the solution being tested over an extended time without deterioration (e.g., bleeding, break-down, etc.) of the indicator means (e.g., visual indicator means) to an extent that would render the device dysfunctional for providing accurate pH and ammonia determinations. Preferably, an extended time refers to minutes, hours, days, weeks, months, or years. Preferably, an extended time refers to days, weeks, months, or years. More preferably, an extended time refers to days, weeks, months, or years. Most preferably, an extended time refers to weeks, months, or years, without deterioration of the indicator means to an extent that would render the device dysfunctional for providing accurate pH and ammonia determinations. Preferably, the stable pH and ammonia indicator means are stable visual indictor means. In particular aspects, the stable visual indicator means comprise pH-sensitive, or ammonia-sensitive dyes (e.g., calorimetric dye indicators) that provide for visual calorimetric determinations of pH and ammonia, respectively.

"Comparison means," as used herein refers to at least one comparison means to be used in combination with the respective indicator means (e.g., visual, calorimetric dyes, etc.) to provide for standardized quantitative determination of solution concentration, in contrast to the limited qualitative information of prior art devices (e.g., such as the AMMONIA ALERT™ card of SEACHEM™, that has, for example, color blocks corresponding to 'presumptive safe,' 'dangerous' or 'toxic' levels). Suitable comparison means may take a variety of forms, including but not limited to charts, curves, tables, graphs, etc. Preferably, the at least one comparison means comprise a linear color-gradient chart, and/or comprise a circular color-gradient or wheel color-gradient chart. In particular embodiments, more than one comparison means is provided for each respective indicator means (e.g., for each respective sensing portion). The comparison means can be integral with or attached (e.g., reversibly attached) to the submersible member, the proximate submersible members, or the attachment base member.

"Movably comparable" as used herein refers to comparison means comprising a comparison chart (e.g., ammonia or pH reference color indicator comparison charts) that is separate or separable from the respective sensing portion, but can be positioned near the respective sensing portion and optionally moved in relation thereto to facilitate visual comparison (e.g., comparative matching of a color bar or color-gradient chart with the indicator color of the respective sensing portion.

"Relational means," as used herein in the context of quantitatively determining total ammonia ($NH_3$ plus $NH_4^+$), refers to relational means (e.g., charts, graphs, tables, formulas, algorithms, etc.) to facilitate quantitative determination of total ammonia ($NH_3$ plus $NH_4^+$), based on the visual indicators of solution ammonia and pH, in combination with the respective quantitative ammonia and pH comparison means.

Aspects of the present invention relate generally to methods and devices for measuring the status of an aqueous environment (e.g., freshwater and saltwater). Particular aspects provide novel methods and devices for proximate quantitative measurement of pH, and ammonia, enabling accurate quantitative determination of 'total ammonia' ($NH_3$ plus $NH_4^+$) in a solution; specifically, by proximate, simultaneous and continuous quantitative measurement of solution pH and ammonia ($NH_3$). The methods provide a substantial advantage over relatively inaccurate, qualitative prior art devices, and can be used in freshwater and saltwater.

Preferred aspects comprise detection means having visual indicator means (e.g., calorimetric dyes, etc.) in combination with comparison means to provide for standardized quantitative determination of solution concentration, in contrast to the limited qualitative information (e.g., presumptive safe, dangerous or toxic levels) of prior art devices (e.g., such as the AMMONIA ALERT™ card of SEACHEM™). Quantification of ammonia is important, because it enables users to accurately know the toxic ammonia concentration and reach conclusions about the risk level, potential problems and toxicity, and with respect to nitrate/nitrite issues of the tested aqueous solution (e.g., in the context of organisms (e.g., fish, plant life, etc.) being held or reared in an aquarium, pond, container, etc.). Additionally, quantification of ammonia enables the determination of solution 'total ammonia' ($NH_3$ plus $NH_4^+$). Significantly, by proximate, combined ammonia and pH measurements, quantitative determinations of both parameters are made simultaneously, in the same or proximate solution place, and with exposure to the same aqueous environment (e.g., temperature, interfaces, surfaces, vegetation, sources of air or other gases, etc), thereby providing a more accurate determination of the solution status, which is particularly important for accurate, reliable determination of 'total ammonia.'

In preferred embodiments, ammonia and pH sensor portions are proximately combined on a single submersible member, or combined on a plurality of proximate, coordinately-submersible members, to enable measurement and quantitative determination of both pH and ammonia concentration at the same time, temperature and position of an aqueous environment), providing a more accurate quantitative determination of the solution status, particularly that of 'total ammonia' ($NH_3$ plus $NH_4^+$), than has heretofore been possible. The sensor portions can, in each case, be integral with the submersible member or proximate submersible members, attached to the submersible member or proximate submersible members, or reversible attached to the submersible member or proximate submersible members to facilitate replacement or attachment of additional sensors (e.g., to replace a sensor, and/or to add an additional ammonia and/or pH sensor covering a different or overlapping range of solution ammonia concentrations and/or pH ranges, respectively). In particular aspects, a visual ammonia indicator comparison means is attached (e.g., reversibly) to or integral with the submersible member or proximate submersible members. The ammonia indicator means is comparable with the continuous visual indicator of the ammonia-sensing portion for standardized quantitative determination of solution ammonia concentration. In particular embodiments, a visual pH indicator comparison means is attached (e.g., reversibly) to or integral with the submersible member or proximate submersible members. The pH indicator means is comparable with the continuous visual indicator of the pH-sensing portion for standardized quantitative determination of solution pH.

In preferred embodiments, the continuous visual indicator of the ammonia-sensing portion, and/or the continuous visual indicator of the pH-sensing portion, comprises a calorimetric dye indicator. In particular aspects, the visual ammonia indicator comparison means comprises an ammonia reference color indicator comparison chart integral with or attached (e.g., reversibly) to the submersible member or proximate submersible members. Alternatively, the visual ammonia indicator comparison means may comprise an ammonia reference color indicator comparison chart that is separate from, but movably comparable to the ammonia-sensing portion of the submersible member or proximate submersible members. Preferably, the ammonia reference color indicator comparison chart comprises a color-gradient indicator comparison chart (e.g., linear color-gradient chart, or a circular or wheel color-gradient chart).

In preferred embodiments, the visual pH indicator comparison means comprises a pH reference color indicator comparison chart integral with or attached (e.g., reversibly) to the submersible member or proximate submersible members. Alternatively, the visual pH indicator comparison means comprises a pH reference color indicator comparison chart that is separate from, but movably comparable to the pH-sensing portion of the submersible member or proximate submersible members. Preferably, the pH reference color indicator comparison chart comprises a color-gradient indicator comparison chart (e.g., a linear color-gradient chart, or a circular or wheel color-gradient chart).

In particularly preferred embodiments, the combination pH and ammonia measuring devices for simultaneous, continuous measurement of solution pH and ammonia further comprise relational means (e.g., charts, curves, tables, graphs, etc) for quantitatively determining total ammonia ($NH_3$ plus $NH_4^+$), based on relating the visual indicator of solution ammonia concentration and the visual indicator of solution pH, in combination with the respective quantitative ammonia and pH comparison means. Such indirect, relational embodiments provide for accurate determination of pH, ammonia, and 'total ammonia.' Alternatively, the inventive combination devices can be used for directly determining total ammonia concentration. For such direct applications the submersible member or proximate submersible members (e.g., strip sensors) are put into a test sample aliquot, along with an added agent to increase the pH, and the inventive sensors then provide a measure of total ammonia; because the ammonium ion ($NH_4^+$) is converted to ammonia ($NH_3$). The use of a plurality of ammonia sensors of different or overlapping range is particularly preferred in such direct embodiments, because in conjunction with the higher pH, the ammonia levels measured will be total ammonia levels that are much higher than the ammonia present in most typical aqueous environment. For example, a bromocresol green (BCG) sensor, or chlorophenol red CPR) type sensor is employed. Additionally, even for such direct measurement of total ammonia, the presence of a proximate pH sensor in the same sample as is being tested for total ammonia has considerable value for confirming that the pH is sufficiently high to adequately perform the reliable total ammonia test. Without the proximate pH sensor, the user would not otherwise know that the pH is sufficiently high without the additional need for independent measuring the adjusted solution with a separate non-proximate pH sensing means and the attendant uncertainties.

Significantly, the inventive methods and devices do not require removal of a test sample, or a plurality thereof to conduct analyses, thus eliminating inhomogeneous sampling and testing errors and discrepancies that occur where one or more smaller solution test samples are taken, serially in time, from different special positions within a larger aqueous environment to be tested at different times, temperatures, pH, and/or proximity to other sources of inhomogeneity (e.g., interfaces, surfaces, vegetation, sources of air or other gases, etc) in the aqueous environment. Accurate status determinations are particularly important in making reliable total ammonia measurements and determinations based on the pH and $NH_3$ levels.

Preferred embodiments provide combination pH and ammonia measuring devices for simultaneous, continuous measurement of solution pH and ammonia, comprising a unique ultra-high sensitivity visual ammonia sensor, heretofore not described, capable of providing accurate measures of ammonia in a lower ppm range that could be previously detected, such that the measurements can be indicative of a developing problem and/or potential toxic condition that was heretofore not predictable. In preferred embodiments of the invention, the enhanced sensitivity to ammonia detection is provided by immobilizing one or more indicator dyes in porous matrix polytetrafluoroethylene (PTFE). For example, an indicator dye is immobilized in a composite supported microporous PTFE medium, comprising a PTFE microporous membrane having secured directly to at least one face thereof a PTFE web of microfibres. In preferred aspects, bromophenol blue (BPB) dye is immobilized in a special porous matrix polytetrafluoroethylene (PTFE) material (ZEFLUOR™, Pall Gelman, Ann Arbor, Mich.; see U.S. Pat. No. 5,366,631 entitled "Composite, Supported Fluorocarbon Media," and incorporated herein by reference in its entirety; see also U.S. Pat. Nos. 3,953,566 and 4,187,390 (describing PTFE membranes) and U.S. Pat. No. 4,716,074 (describing PTFE web), all of which are incorporated herein by reference in their entirety), or the functional equivalent thereof, to form an ammonia sensor, which yields a higher ammonia sensitivity (e.g., in the range of about 0.005 to about 0.1 ppm) than previously reported (e.g., having a significantly higher sensitivity than BPB in another PTFE substrates, such as TEFLON™ tape produced by St. Gobain).

ZEFLUOR™ (PTFE with a PTFE support) comprises a web of fluoropolymeric microfibers secured to a fluoropolymeric microporous membrane. The composite, supported microporous membrane is free of any adhesive components, the membrane being secured (by bringing the material to "fusion temperature" and application of sufficient pressure to achieve binding of the membrane to the microfiber material) to the web solely at the interfaces of the membrane and the web (see U.S. Pat. No. 5,366,631). ZEFLUOR™ is available in a variety of pore sizes and thicknesses: for example, 0.5, 1, 2, 3 μm pores, with the following respective thickness 0.5 μm (178 μm; 7 mils thick); 1 μm (165 μm; 6.5 mils thick); 2 and 3 μm (152 μm; 6 mils thick) and 5 μm (127 μm; 5 mils thick). ZEFLUOR™ and ZYLON™ (unsupported PTFE) offer low chemical background for highly sensitive determinations. In particular aspects, Gelman 3 μm Zefluor PTFE (Teflon) microporous membranes are used, having a microporous Teflon layer approximately 15 μm thick mounted onto a 165 μm thick Teflon macroporous substrate, for a total thickness of 180 μm. The porosity of the 15 μm microporous layer is calculated to be 44%, based on void volume information obtained from Gelman.

Therefore, while in particular aspects, the ammonia-sensing portion of the inventive devices is suitable to detect ammonia in the range of about 0.05 to about 0.5 ppm, or about 0.05 to about 1.0 ppm, preferably, the ammonia-sensing portion of the inventive devices is suitable to detect ammonia in the range of about 0.005 to about 0.1 ppm, or about 0.005 to about 0.05 ppm, or from about 0.005 to 0.05 ppm. Significantly, provision of such ultra-high sensitivity ammonia sensors (e.g., in the range of about 0.005 to about 0.1 ppm, or about 0.005 to about 0.05 ppm, or from about 0.005 to 0.05 ppm, or about 0.005 ppm to about 0.01 ppm, or from 0.005 ppm to 0.01) in combination, or proximate combination, with a pH sensor has not previously been described. Therefore, in particular embodiments, the device is capable of detecting ammonia levels as low as about 0.005 ppm.

In particular aspects, the inventive devices may comprise a plurality of pH or ammonia sensors representing different detection ranges (e.g., a plurality of ammonia sensors, representing different ammonia detection ranges). For example, in particular aspects the device comprises a pH sensor portion, in combination with two ammonia sensing portions, where the ammonia sensing portions are sensitive to different or overlapping concentration ranges of ammonia. As stated above, the sensor portions can, in each case, be integral with the submersible member or proximate submersible members, can be attached to the submersible member or proximate submersible members, or can be reversible attached to the submersible member or proximate submersible members to facilitate replacement or attachment of additional sensors (e.g., an additional ammonia sensor covering a different or overlapping range of solution ammonia concentrations). Use of two or more visual sensors (e.g., ammonia sensors) of different but overlapping ranges of ammonia sensitivity not only provides a wider range of measurable solution ammonia concentration, but also affords increased accuracy and reliability of measures by having two color-matches to pinpoint and determine the ammonia concentration.

Particular aspects provide a combination pH and ammonia measuring device as described and disclosed herein, comprising a plurality of submersible ammonia-sensing portions, wherein at least two of the ammonia sensing portions have different ammonia sensitivities. In particular embodiments, the at least two ammonia sensing portions having different ammonia sensitivities each have a different sensitivity range selected from the ammonia sensitivity range group consisting of about 0.05 to about 0.5 ppm, about 0.05 to about 1.0 ppm, about 0.005 to about 0.1 ppm, about 0.005 ppm to about 0.05 ppm, about 0.005 ppm to 0.05 ppm, about 0.005 to about 0.01, or from about 0.005 to 0.01. Certain embodiments comprise at least three submersible ammonia-sensing portions each having a different ammonia sensitivity or sensitivity range. In particular implementations, the at least three ammonia sensing portions having different ammonia sensitivities each have a different sensitivity range selected from the ammonia sensitivity range group consisting of about 0.05 to about 0.5 ppm, about 0.05 to about 1.0 ppm, about 0.005 to about 0.1 ppm, about 0.005 ppm to about 0.05 ppm, and about 0.005 ppm to 0.05 ppm.

Therefore, certain embodiments comprise two or three ammonia sensor, and/or pH sensor elements into a signal device with each sensor of a given sensor type (e.g., pH or ammonia) having a different sensitivity, and further showing a different color in response to a given level of NH3 (or to a given pH value in the case of multiple pH sensors having different sensitivities or different ranges thereof).

According to particular aspects, such 'compound range' embodiments provide at least two primary advantages. First, the useful sensing range of the devices is increased, enabling readout over a wider scale. Second, the interpretive ease and accuracy of the readout is substantially enhanced, because it is easier and more accurate to match a pair, for example, of different colors of two sensors against a reference color-chart with respective paired colors, than it is to discriminate a single sensor's color against a chart with subtle hue differences between close ammonia concentrations, or close pH values. These aspects provide a solution to a rather common problem with single sensors. For example, prior art pH and NH$_3$ sensors don't exhibit marked changes through different colors (e.g. from yellow to green to blue). They only shift from a baseline yellow to very little green and then darker shades of green with increasing ammonia.

In particular aspects, the inventive combination pH and ammonia measuring devices for simultaneous, continuous measurement of solution pH and ammonia comprise a submersible member, or a plurality of proximately connected, coordinately-submersible members, suitable to be at least partially submersible in a solution. Solution status sensors (e.g., pH and/or NH$_3$) are integral with, attached to, or reversibly attached to the submersible member or to the plurality of proximate submersible members, such that submersion of the submersible member or the plurality of proximate submersible members enables continuous coordinate proximate submersion of the integral and/or attached sensors into the solution environment to be tested. In particular aspects, the submersible member or the plurality of proximate submersible members comprise one or more submersible strips, with the sensor components integral with, and/or attached to (e.g., reversibly attached to) the submersible strip or proximate submersible strips. In particular aspects, sensors can be replaced on a submersible strip, or additional sensors can be added to a strip.

In particular preferred aspects, the combination pH and ammonia measuring devices for simultaneous, continuous measurement of solution pH and ammonia comprise an optionally attachable attachment base member (e.g., immersible indicator card) that may be nonsubmersible, or optionally submersible or partially submersible. In certain of such embodiments, the above-described submersible member or proximate submersible members having the sensor means, are reversibly attachable to the attachment base member, so that the submersible member or proximate submersible members can be detached (e.g., for aesthetic, or spatial reasons) from the attachment base member for coordinate submersion of the sensors in the solution, without the presence of the larger attachment base member. Therefore, in particular embodiments, the submersible member or proximate submersible members (e.g., strips having pH and ammonia sensor portions) can be attached to a companion attachment base member (e.g., immersible-indicator card) for convenient reading by color-matching with a comparative standard indicator guide (e.g., color chart) located on the attachment base. Alternatively, and uniquely, the submersible member or proximate submersible members (e.g., strips having pH and ammonia sensor portions) can be detached from the attachment base member (e.g., from the immersible-indicator card) for independent use, providing for a smaller and less obtrusive combination sensing device. In such alternative embodiments, the comparative standard indicator chart, or charts, can be held and/or moved in the proximity of the respective sensors for color-matching for making a quantitative determination of the ammonia and pH values. Additionally, the removable/detachable, submersible member or proximate submersible members (e.g., strip-sensor component) enables the sensors to be placed, if desired, in a small volume test sample for discrete sample testing, for instance, of an aliquot put in a small volume test tube. Alternatively, the submersible member or proximate submersible members can be detached from the attachment base member and used in the primary solution, where a user desires less obtrusive measuring means (e.g., in a aquarium, landscaping ponds, etc.).

For purposes of the present invention, the submersible member, the proximate coordinately-submersible members, or the attachment base member can be totally or partial submersed, the only requirement being that they are submersible to an extent sufficient to allow for coordinate submersion of the integral or attached sensors. In particular embodiments, the measuring devices further comprise at least one positioning element for positioning the device within the test solution. In certain embodiments, the at least one positioning element articulates with the submersible member or proximate coordinately submersible members to position the member or members so that they can be viewed by a user. Alternatively, the positioning element articulates with the attachment base member. In certain embodiments, the position element articulates with an orifice in the submersible member and/or the attachment base member. A variety of different positioning elements are suitable for use in positioning the submersible member or attachment base member for viewing by a user, including buoyancy elements (e.g., floats), suction cups, adhesives, hooks, clips, snaps, tethers, magnets, etc. For example, a float or suction cup may be articulated with an orifice in the top of a submersible member, or attachment base member to position the device at a convenient viewer-friendly position within the solution being tested.

In particular aspects, as discussed briefly above, more accurate and reliable visual determinations are enabled by providing a color-gradient indicator approach, rather than merely color-block matching. Color-gradient indicator comparison charts enable the eye to make more precise color matching, whereas block color matches are difficult to perform when the color of the sensor does not exactly match a provided indicator color-block color. In particular aspects, even more accurate and precise color matching is afforded by providing a large color gradient that can be moved or changed in presentation with respect to the respective sensor. Preferably, the color-gradient chart is or comprises at least one of a linear color gradient, or a circular or 'wheel'-gradient.

As will be appreciated in the relevant art, bright light, in particular sunlight, as might be encountered when using sensors in outdoor ponds and pools, may pose a problem in that direct exposure to sunlight may cause a significant degradation of sensors over time. Therefore, according to particular aspects of the present invention, protection from sunlight or otherwise even bright aquarium lighting is of considerable significance in providing a viable product for outdoor applications.

Particular embodiments, therefore, associate or incorporate at least one light blocking aspect or member to reduce the effect of light (e.g., aquarium lights) that might cause bleaching of the sensor dyes, or the inks used to create the comparative standard indicator guide (e.g., color chart located on the attachment base). In particular aspects, the light blocking aspect encompasses a light-absorbing or reflective shield or shroud around the device (e.g., prior art devices or those disclosed herein) with an unobscured region for viewing the device sensors. Alternatively, light absorbing or reflective paints or coatings are applied to the backside, or a non-viewing side of the submersible elements. In yet further aspects, therefore, UV absorbing agents (e.g., art-recognized UV blocking films) of such types commonly used in polymers and coatings in the printing industry to reduce bleaching or fading of inks and dyes exposed to light, are associated with, or incorporated into the submersible elements or specifically the ammonia sensing or pH sensing portions (e.g., placed over or around the sensors in a manner that yet allows circulation of the solution or test water, etc., around the sensor) to provide shielding benefit. Additional aspects provide for association and/or incorporation of visible light blocking agents.

In additionally aspects, reflective films, such as metalized polymers (e.g., Mylar) are used for light shielding and have been shown by applicants to be significantly beneficial in practicing aspects of the present invention. For such reflective films, the effectiveness was determined to be proportional to the density of the light absorbing or reflective aspects thereof.

In preferred aspects, a cover over and/or around the sensors using totally light-blocking material is used. In particular aspects, the cover comprises a black plastic hood or shroud placed over the top of the sensor device. In additional aspects, a black plastic cylinder encompassing the sensor device is used (e.g., that the sensor device slides down inside). Although, such 'light protected' sensors preclude casual viewing because they at least partially obscure the sensor, they are nonetheless useful, particularly where they can be easily lifted to allow for casual viewing of the sensor, and particularly where such sensors are significantly longer lasting that non-protected counterparts. Additionally, such sensors are particular valuable where infrequent viewing of the sensor is sufficient, such as in more stable aqueous environments.

Therefore, according to additional aspects, there are many shapes, forms, and configurations for light shielding means that can be designed which meet the two constraints of UV and/or visible light-blocking and yet allowing water to reach and circulate around the sensor (e.g., of both art-recognized and presently disclosed sensor devices).

Suitable pH indicator dyes are known in the relevant art, and preferred exemplary pH indicator dyes (along with respective effective pH ranges) include, but are not limited to: Bromocresol Purple pH 5.2-6.8); Bromothymol Blue (pH 6.0-7.6); Phenol Red (pH 6.8-8.4); Thymol Blue (pH 8.0-9.6). Various pH-sensing materials of suitable stability (e.g., non-bleeding, or substantially so) for use in the present inventive continuous measurement embodiments are known in the art. In particular aspects the submersible pH-sensing portions comprise non-bleeding pH indicator strips (e.g., COLOR-PHAST® pH 6.5-10.0; made by EMD Chemicals, Inc. Gibbstown, N.J., USA; or other polymer-based pH sensors such as those made by "ph-ion", and "Livemeter"). Various measurable pH ranges (and respective sensor portions and indicator means) are encompassed within the scope of the present invention, including but not limited to: about pH 5 to about pH 9.5; about pH 5.5 to about pH 9; about pH 6 to about pH 9; about pH 6.5 to about pH 8.7. Preferably, the pH range is about pH 6 to about pH 9; or about pH 6.5 to about pH 8.7. Preferably, the pH range is about pH 6 to about pH 9. Preferably the range is one suitable to span freshwater and saltwater conditions.

With respect to visual ammonia sensing, regarding the ranges of use with different dyes, pieces of sensor material large enough for viewing are exposed in an environment to be monitored for ammonia. In addition to bromophenol blue (BPB), stable sensor compositions comprising bromocresol green (BCG) as the ammonia-sensitive indicator dye exhibit, in solution, a reversible color change from yellow towards blue-green to finally a blue hue when exposed to ammonia of respectively increasing concentration (e.g., in the range of 0 to about 5 ppm or greater). Likewise, chlorophenol red (CPR) has utility as an ammonia sensitive indicator dye, and exhibits a reversible color change in solution from orange towards magenta and eventually a purple hue when exposed to ammonia of increasing concentration (e.g., in the range of 0 to about 10 ppm or greater). Sensor material can be immersed directly into aqueous samples for monitoring ammonia. In particular aspects the sensors are used for sensing ammonia in air. Preferably, the sensor material (dye substrate) is PTFE (e.g., TEFLON®).

In particular embodiments, the ammonia sensors are made as described in U.S. patent application Ser. No. 09/157,209 (pub. no. 20030003589), which in incorporated by reference herein in its entirety. Briefly, the sensor composition is made from an ammonia sensitive indicator dye and a solid phase, preferably a PTFE solid phase (e.g., film form). The sensor compositions are constructed by administering ammonia-sensitive indicator dye(s) in a non-aqueous solvent to a solid-phase PTFE substrate such that the dye is deposited on the solid phase in a form insoluble to aqueous-based solvents (Id).

For example, ammonia-sensitive indicator dyes are dissolved in an appropriate (non-aqueous) solvent that will wet, penetrate, or dissolve the PTFE substrate. Preferred solvents include, but are not limited to tetrahydrofuran, ethanol, and methanol. The solvent serves as a "carrier" of the ammonia-sensitive indicator dye (or combinations thereof) for application to PTFE solid phase substrates. Exemplary preparations of dye solutions for preparing indicator films for applications involving visual detection are: (a) bromocresol green (Aldrich #11,435-9), 100 mg dissolved in 20 ml methanol; (b) chlorophenol red (Aldrich #19,952-4), 100 mg dissolved in 20 ml methanol; and (c) phenol red (Aldrich #11,452-9), 100 mg dissolved in 20 ml methanol. Generally, solutions for preparing an ammonia-sensitive indicator dye for application to a PTFE film that will be used for optical measurements are made, for example, by dissolving 20 mg of the corresponding dye in 20 ml methanol. Other exemplary suitable solution preparations that have been made include chlorophenol red (Aldrich #19,952-4), 22 mg dissolved in 10 ml tetrahydrofuran, bromophenol blue (Aldrich #11,439-1), 10 mg dissolved in 10 ml Ethanol, and bromocresol green (Aldrich #11,435-9), 20 mg dissolved in 10 ml tetrahydrofuran.

PTFE (Teflon®) is the preferred solid phase substrate. The hydrophobicity of the PTFE provides a strong non-covalent bond to bond the dyes. Ammonia diffuses through PTFE easily, and PTFE material can be easily fabricated and cut into appropriate shapes or configurations for particular sensing applications. PTFE tapes and film materials from several different manufacturing sources have been used to fabricate inventive ammonia sensor compositions. Use of preformed solid-phase films, membranes, or tapes affords simple and economical manners of fabricating of ammonia sensor compositions. A porous PTFE form is preferred, to promote the faster penetration of the gaseous compound into the polymer and reaction with the ammonia sensitive indicator dye immobilized therein. Exemplary PTFE material manufactures whose products have been used as PTFE substrates for sensor compositions in the form of a film include, for example, PTFE thread seal tapes from Plastomer Products Division (Newtown, Pa.), or Furon (Hoosick Falls, N.Y.), and porous PTFE films from Gore-Tex (Elkton, Md.). More preferably, as described for the first time herein, the sensor material is comprises porous matrix polytetrafluoroethylene (PTFE) having an ammonia-sensitive immobilized dye, the immobilized dye suitable to provide for a calorimetric determination of ammonia level. Preferably, the ammonia-sensitive immobilized dye is BPB dye. Most preferably, the porous matrix polytetrafluoroethylene (PTFE) comprises a composite supported microporous PTFE medium, comprising a PTFE microporous membrane having secured directly to at least one face thereof a PTFE web of microfibres (e.g., ZEFLUOR™, Pall Gelman, Ann Arbor, Mich.; see U.S. Pat. No. 5,366,631 entitled "Composite, Supported Fluorocarbon Media," and incorporated herein by reference in its entirety; see also U.S. Pat. Nos. 3,953,566 and 4,187,390 (describing PTFE membranes) and U.S. Pat. No. 4,716,074 (describing PTFE web), all of which are incorporated herein by reference in their entirety), or the functional equivalent thereof). Preferably, the detectible range of ammonia using such porous matrix polytetrafluoroethylene (PTFE) comprises a range of about 0.005 to about 0.1 ppm, providing an ultra-sensitive ammonia detection device that is suitable to detect low amounts of ammonia in either solution, or in air.

A preferred method of fabrication is to dip the PTFE material (e.g., 2 cm to 5 cm wide PTFE strips) into a bath of an indicator dye stock solution. An "indicator stock solution" comprises an ammonia sensitive indicator dye (or combinations thereof) dissolved in a non-aqueous solvent. This allows ammonia sensitive indicator dye to adhere to the solid phase PTFE to form a "wet" sensor composition. The wet sensor composition is dried at room temperature, or aided with forced air or a drier to facilitate solvent evaporation. The sensor composition (now dried) is then immersed in a fuming 1N-hydrochloric acid solution for 10 minutes. This is followed by a final rinse by immersion in water for 2 minutes. The sensor composition is then left to dry.

Therefore, aspects of the present invention also provide an ultra-sensitive ammonia detection device for detecting ammonium and/or volatile amines in a gas or liquid state, comprising an ammonia-sensitive indicator dye (e.g., BPB) having measurable spectral characteristics immobilized in or on a solid substrate, whereby exposure to a compound causes a change in spectral characteristics of the dye. Preferably, the solid substrate is porous matrix polytetrafluoroethylene (PTFE) (e.g., comprising a composite supported microporous PTFE medium, comprising a PTFE microporous membrane having secured directly to at least one face thereof a PTFE web of microfibres). The PTFE-based ultra-sensitive sensors may be applied on an object or inside a vessel for the purpose of detecting the presence of particular chemical compounds, such as ammonia in the liquid or vapor phase, in the environment to which the film is exposed.

Exemplary Preferred Embodiments

Exemplary embodiments of the present invention can be better understood with reference to FIGS. 1A-1D, and FIG. 2.

FIGS. 1A-D show exemplary embodiments of a combination pH and ammonia measuring device for simultaneous, continuous measurement of solution pH and ammonia according to particular aspects of the present invention. FIGS. 1A, 1B, 1C and 1D show a combination sensor strip (submersible member having pH and ammonia-sensing means) as a standalone sensor strip (FIGS. 1A and 1D), and as reversibly attached to a sensor card (attachment base member) having integral or attached color charts (FIGS. 1B and 1C).

FIG. 1C shows an attachment base member 12, having attached thereto a submersible member 10. Alternatively, a plurality of proximately connected, coordinately-submersible members, reversibly attachable to the attachment base member 12, and suitable to be at least partially submersible in a solution could be used. Also shown is at least one submersible ammonia-sensing portion 4 integral with or attached to the submersible member 10 or proximate submersible members, the at least one ammonia-sensing portion 4 having stable detection means (e.g., immobilized dye) suitable to provide for a continuous visual indicator of solution ammonia concentration. There is at least one submersible pH-sensing portion 2 integral with or attached to the submersible member 10 or proximate submersible members, the at least one pH-sensing portion 2 having stable detection means (e.g., immobilized dye) suitable to provide for a continuous visual indicator of solution pH. Additionally shown is a visual ammonia indicator comparison means 8 (e.g., color chart), attached to or integral with the attachment base member 12, and comparable with the continuous visual indicator of the at least one ammonia-sensing portion 4 for standardized quantitative determination of solution ammonia concentration. There is also a visual pH indicator comparison means 6, (e.g., color chart), attached to or integral with the attachment base member 12, and comparable with the continuous visual indicator of the at least one pH-sensing portion 2 for standardized quantitative determination of solution pH. The dark area 14 in this particular exemplary embodiment corresponds to an aperture 14 through the submersible member 10, the aperture articulatible with a positioning means (not shown), such as a floatation member, or container attachment member (e.g., suction cup, etc.).

FIG. 2 shows, according to particular aspects of the present invention, the exemplary detachable combination pH and ammonia measuring device embodiment of FIG. 1D (standalone sensor strip), being used to continuously measure pH and ammonia in an aqueous environment (e.g., aquarium, pool, hot tub, lake, river, pond, manufacturing container, etc.). The standalone sensor strip comprises a submersible member 10. Alternatively, a plurality of proximately connected, coordinately-submersible members could be used. The standalone sensor strip additionally comprises at least one submersible ammonia-sensing portion 4 integral with or attached to the submersible member 10 or proximate submersible members, the at least one ammonia-sensing portion 4 having stable detection means (e.g., immobilized dye) suitable to provide for a continuous visual indicator of solution ammonia concentration. The standalone sensor strip further comprises at least one submersible pH-sensing portion 2 integral with or attached to the submersible member 10 or proximate submersible members, the at least one pH-sensing portion 2 having stable detection means (e.g., immobilized dye) suitable to provide for a continuous visual indicator of solution pH. The dark area 14 in this particular exemplary embodiment corresponds to an aperture 14 through the submersible member 10, the aperture articulatible with a positioning means (not shown), such as a floatation member, or container attachment member (e.g., suction cup, etc.).

FIG. 3 shows, according to further aspects of the present invention, another exemplary combination pH and ammonia measuring device embodiment. The exemplary embodiment of FIG. 3, has two separable members: a submersible main body carrier or member 16 (in the instance formed of a transparent plastic) comprising a reference color-chart 8 included in a slot therein (or retaining means thereon), and an ammonia sensing portion 4 affixed to the outside of the carrier member 16; and a pH sensing member 10 comprising a pH sensing portion 2. The color-chart 8 within the main body carrier or member 16 is slidably removable therefrom (e.g., for users not wanting to see anything more than the sensor in their aquarium). The pH sensing portion 2 on the pH sensing member 10 inserts into, and/or appends from the main body carrier or member 16. The pH sensing member 10 is easily removed and replaceable (e.g., as a replaceable cartridge), for example, in embodiments wherein the service life of the pH sensing member 10 is not as great as that of the an ammonia sensing portion 4 affixed to the outside of the carrier member 16, and thus optimally is periodically changed without change of the main body carrier or member 16 comprising the ammonia sensing portion 4 affixed thereto. The exemplary pH indicator reference color chart 6 is a continuous color gradient chart, starting at a position corresponding to clock position 9:00 and proceeding clockwise in this instance around to clock position 9:00. Likewise, the exemplary ammonia indicator reference color chart 8 is a continuous color gradient chart, starting in this instance at a position corresponding to clock position 3:00 and proceeding clockwise to clock position 9:00. The changes in color gradient are illustratively indicated in the drawing by changing stippling patterns.

With respect to the exemplary inventive ammonia sensor of FIG. 3, user viewing is preferably by looking 'front-on' (e.g., perpendicularly facing the sensor). In alternate embodiments (FIG. 4), at least one of the ammonia sensing and/or pH sensing portions (e.g., sensor strips) is suitably configured (e.g., of sufficient length and structure) to extend (e.g., wrap, encircle, etc.) horizontally around, for example, the sides of the main body member (e.g., or around the main body perimeter or portions thereof, regardless of the shape or configuration of the overall main body) so that the at least one of the ammonia sensing and/or pH sensing portions can be seen from different angles (e.g., from the sides, back, etc.) by a user. The configuration of the sensor main body member, or of a side of the main body member can be flat, curved, raised concave, convex, etc. Such novel embodiments have several advantages not known in the respective art. For example, mounting of such embodiments of the device on the side of an aquarium (e.g., the frontal larger dimension of the sensor facing the side of the aquarium) not only provides for a front-on user view of the sensor from the side of the aquarium different, but additionally provides a benefit that in a user view of this sensor from the front of the aquarium (e.g., a full frontal view of the aquarium, but only a side view of the sensor as so-disposed), the viewable side portion is relatively small (compared to a perpendicular view of the face of the sensor, or to prior art devices) and all that would be seen is a small piece (e.g., about ⅛") of sensor on the edge of the device. Such an edge view, according to particular aspects of the present invention, is aesthetically very unobtrusive (not blocking viewing of the contents of the aquarium), but yet allows viewing of a sufficient portion (e.g., about ⅛"), such that if this sensor edge view indicated that the aquarium conditions (e.g., pH and/or ammonia concentration) were 'off' or problematic, the user could check the conditions more carefully by viewing the sensor face-on from the side of the tank. According to particular aspects, this is a substantial benefit not provided in the prior art, which consists of products that are planar, and can only be viewed frontally, such that in functional operation of such prior art sensor, all of the sensor area (e.g., all the sensor material and color-indicator charting, etc) is viewable and is simultaneously obscuring the user view of the aquarium contents by an equivalent area.

According to various aspects, the objective of enabling sensor viewing of pH or ammonia sensor devices in generally, including art-recognized devices and those presently disclosed, from different user angles or positions to reduce obscuring of the view of the aquarium contents during functional operation of the sensor, is accomplished in various ways, including but not limited to: wrapping the sensor partially or completely around, for example, a clear cylinder or tube; or using one or more mirrors, lenses, or prism-like elements (e.g., plastic lenses or prism-like elements) to reflect a sensor image, or portion thereof, over a wider angle or dimension.

Additional Exemplary Embodiments

Particular aspects provide a combination pH and ammonia measuring device for simultaneous, continuous measurement of solution pH and ammonia, comprising: a submersible member, or a plurality of proximately connected, coordinately-submersible members, suitable to be at least partially submersible in a solution; at least one submersible ammonia-sensing portion integral with or attached to the submersible member or proximate submersible members, the at least one ammonia-sensing portion having stable detection means suitable to provide for a continuous visual indicator of solution ammonia concentration; at least one submersible pH-sensing portion integral with or attached to the submersible member or proximate submersible members, the at least one pH-sensing portion having stable detection means suitable to provide for a continuous visual indicator of solution pH; a visual ammonia indicator comparison means, comparable with the continuous visual indicator of the at least one ammonia-sensing portion for standardized quantitative determination of solution ammonia concentration; and a visual pH indicator comparison means, comparable with the continuous visual indicator of the at least one pH-sensing portion for standardized quantitative determination of solution pH. Preferably, the continuous visual indicator of the at least one ammonia-sensing portion comprises a calorimetric dye indicator. Preferably, the continuous visual indicator of the at least one pH-sensing portion comprises a calorimetric dye indicator.

In particular aspects, the visual ammonia indicator comparison means comprises an ammonia reference color indicator comparison chart integral with or attached to the submersible member or proximate submersible members. Alternatively, the ammonia reference color indicator comparison chart is separate from, but movably comparable to the at least one ammonia-sensing portion of the submersible member or proximate submersible members. Preferably, the ammonia reference color indicator comparison chart comprises a color-gradient indicator comparison chart (e.g., a linear color-gradient chart, or a circular or wheel color-gradient chart).

In particular aspects, the visual pH indicator comparison means comprises a pH reference color indicator comparison chart integral with or attached to the submersible member or proximate submersible members. Alternatively, the pH reference color indicator comparison chart is separate from, but movably comparable to the pH-sensing portion of the submersible member or proximate submersible members. Preferably, the pH reference color indicator comparison chart comprises a color-gradient indicator comparison chart (e.g., a linear color-gradient chart, or a circular or wheel color-gradient chart).

In particular embodiments, the combination pH and ammonia measuring device comprises an ammonia-sensing portion suitable to detect ammonia in the range of about 0.05 to about 0.5 ppm, about 0.05 to about 1.0 ppm, about 0.005 to about 0.1 ppm, about 0.005 ppm to about 0.05 ppm, about 0.005 ppm to 0.05 ppm, about 0.005 to about 0.01 ppm, or about 0.005 to 0.01 ppm. Preferably, the ammonia-sensing portion is suitable to detect ammonia in the range of about 0.005 to about 0.1 ppm. In preferred embodiments, the ammonia-sensing portion comprises a bromophenol blue dye in a porous PTFE support.

In further aspects, the combination pH and ammonia measuring device, further comprises relational means for quantitatively determining total ammonia ($NH_3$ plus $NH_4^+$), based on the visual indicator of solution ammonia concentration and the visual indicator of solution pH, in combination with the respective quantitative ammonia and pH comparison means.

Yet further embodiments provide a combination pH and ammonia measuring device for simultaneous, continuous measurement of solution pH and ammonia, comprising: an attachment base member; a submersible member, or a plurality of proximately connected, coordinately-submersible members, reversibly attachable to the attachment base member, and suitable to be at least partially submersible in a solution; at least one submersible ammonia-sensing portion integral with or attached to the submersible member or proximate submersible members, the at least one ammonia-sensing portion having stable detection means suitable to provide for a continuous visual indicator of solution ammonia concentration; at least one submersible pH-sensing portion integral with or attached to the submersible member or proximate submersible members, the at least one pH-sensing portion having stable detection means suitable to provide for a continuous visual indicator of solution pH; a visual ammonia indicator comparison means, comparable with the continuous visual indicator of the at least one ammonia-sensing portion for standardized quantitative determination of solution ammonia concentration; and a visual pH indicator comparison means, comparable with the continuous visual indicator of the at least one pH-sensing portion for standardized quantitative determination of solution pH. Preferably, the continuous visual indicator of the ammonia-sensing portion comprises a calorimetric dye indicator. Preferably, the continuous visual indicator of the pH-sensing portion comprises a calorimetric dye indicator. In particular aspects, the visual ammonia indicator comparison means comprises an ammonia reference color indicator comparison chart integral with or attached to the attachment base member. Alternatively, the ammonia reference color indicator comparison chart is separate from the attachment base member, but movably comparable to the at least one ammonia-sensing portion of the submersible member or proximate submersible members. Preferably, the ammonia reference color indicator comparison chart comprises a color-gradient indicator comparison chart (e.g., a linear color-gradient chart, or a circular or wheel color-gradient chart). In particular aspects, the visual pH indicator comparison means comprises a pH reference color indicator comparison chart integral with or attached to the attachment base member. Alternatively, the pH reference color indicator comparison chart is separate from the attachment base member, but movably comparable to the at least one ammonia-sensing portion of the submersible member or proximate submersible members. Preferably, the pH reference color indicator comparison chart comprises a color-gradient indicator comparison chart (e.g., a linear color-gradient chart, or a circular or wheel color-gradient chart). In particular embodiments, the ammonia-sensing portion is suitable to detect ammonia in the range of about 0.05 to about 0.5 ppm, about 0.05 to about 1.0 ppm, or about 0.005 to about 0.1 ppm. Preferably, the ammonia-sensing portion is suitable to detect ammonia in the range of about 0.005 to about 0.1 ppm. In preferred embodiments, the ammonia-sensing portion comprises a bromophenol blue dye in a porous PTFE support. In certain aspects, the attachment base member is at least partially submersible in a solution, and the visual ammonia indicator comparison means and the visual pH indicator comparison means are integral with or attached to the attachment base member or to the submersible member or proximate submersible members. Preferred embodiments further comprise relational means (charts, graphs, tables, etc.) to allow for quantitative determination of total ammonia ($NH_3$ plus $NH_4^+$), based on the visual indicator of solution ammonia concentration and the visual indicator of solution pH, in combination with the respective quantitative ammonia and pH comparison means.

In yet further embodiments, at least one of the at least one submersible ammonia-sensing portion or the at least one submersible pH-sensing portion further comprises an antimicrobial agent. Exemplary candidate antimicrobial agents include silver, colloidal silver, silver dioxide, titanium dioxide, Triclosan to inhibit algae, or Thiabendazole-based antimicrobials to inhibit fungi. Preferred are those agents that are stably associated with the submersible sensing portion(s). In certain embodiments the antimicrobial agent consists of a selectively porous barrier material or membrane, or comprises a selectively porous barrier material or membrane, optionally in combination with one or more antimicrobial agents such as those described herein. Preferably, at least one of the at least one submersible ammonia-sensing portion or the at least one submersible pH-sensing portion further comprises an antimicrobial agent.

In preferred aspects, an AEM 5700 antimicrobial solution (e.g., a silane Quaternary Ammonium Salt; namely, 3-(trimethoxysilyl) propyldimethyl octadecyl ammonium chloride); AEGIS ENVIRONMENTS, INC. Midland, Mich.), or the equivalent is used. In certain aspects, a pH sensor portion and/or an ammonia sensing portion is treated by brief immersion of the portion(s) in a solution of this product (e.g., 0.05% to about 10% (w/v)).

In further preferred aspects, the pH sensor and/or the ammonia sensor in enclosed (e.g., encased, sandwiched between, etc) by sealing it between a transparent sheet (e.g., clear plastic sheet), which allows the sensor to be viewed, and a layer of a porous barrier material or membrane, filter, etc (e.g., porous barrier-filter membrane), wherein the porous barrier material (e.g., membrane or filter) is suitable to preclude microbes (e.g., bacteria), from directly contacting the sensor and growing on or in it. In particular aspects, the antimicrobial agent consists of such enclosing of the sensor(s). In additional embodiment, the antimicrobial agent comprises such enclosing of the sensor(s) in combination with one or more other antimicrobial agents (e.g., in combination with an AEM 5700 antimicrobial agent). For embodiments comprising porous barrier material (e.g., membranes, filters, etc.), the barrier material is preferably selected to have pores small enough to keep, for example, bacteria from getting through to the sensor (e.g., pores of 0.1 or 0.2 microns in diameter, or smaller), but having pores large enough to allow for passage of water and ions so that the underlying sensor is exposed or bathed in water or solution and can respond to the pH and/or ammonia changes in the solution (e.g., tank water). In preferred aspects, the barrier membranes are hydrophilic polymers that are wettable, and preferably robust and flexible for easy fabrication, and preferably not readily degraded by bacterial attack. Exemplary preferred barrier membranes include, but are not limited to polyether sulfone (e.g., Supor 100, with 0.1 micron pores (Pall); or similar products available from Millipore and Whatman), nylon, polycarbonate, etc., or combinations thereof. Additionally, aside from the microbial barrier property, particular barrier materials additionally have 'intrinsic' antimicrobial properties (e.g., chemical properties), or are processed to provide antimicrobial properties by inclusion/treatment with antimicrobial agents as described herein. Additionally, Glass (fibrous) or other porous materials such as a ceramic that wet and will allow passage of water are encompassed by the present inventive methods. Membranes made with cellulosics are less preferred because bacteria can digest and eventually breach such membranes).

Additional embodiments of the present invention provide a method for determining the total ammonia concentration in a solution, comprising: submersing, in a solution, a combination pH and ammonia measuring device for simultaneous, continuous quantitative measurement of solution pH and ammonia; and quantitatively determining total ammonia ($NH_3$ plus $NH_4^+$), based on a visual indicator of solution ammonia concentration and a visual indicator of solution pH. Preferably, the combination pH and ammonia measuring device for simultaneous, continuous measurement of solution pH and ammonia are as described herein.

Yet further embodiments provide an ammonia detection device, comprising porous matrix polytetrafluoroethylene (PTFE) having an ammonia-sensitive immobilized dye, the immobilized dye suitable to provide for a calorimetric determination of ammonia level, and wherein the detectible range of ammonia comprises a range of about 0.005 to about 0.1 ppm. Preferably, the ammonia-sensitive immobilized dye is BPB dye. Preferably, the porous matrix polytetrafluoroethylene (PTFE) comprises a composite supported microporous PTFE medium, comprising a PTFE microporous membrane having secured directly to at least one face thereof a PTFE web of microfibres. Additional embodiments provide a method for detecting ammonia in air, comprising exposing the above-described ammonia detection device to air, wherein a calorimetric determination of air ammonia level is, at least in part, afforded. Particular aspects of this method comprise optical sensing to interrogate the color of the ammonia-sensitive immobilized dye. Further embodiments provide a method for detecting ammonia in solution, comprising exposing the above-described ammonia detection device to a test solution, wherein a colorimetric determination of solution ammonia level is, at least in part, afforded. Particular aspects of this method comprise optical sensing to interrogate the color of the ammonia-sensitive immobilized dye.

Yet further methods comprise enhanced sensitivity sensors, comprising porous matrix polytetrafluoroethylene (PTFE) having one or more immobilized indicator dyes to provide for an enhanced colorimetric determination of detected substance. In particular aspects, the porous matrix polytetrafluoroethylene (PTFE) comprises a composite supported microporous PTFE medium, comprising a PTFE microporous membrane having secured directly to at least one face thereof a PTFE web of microfibres.

Additional embodiments provide a combination pH and ammonia measuring device as otherwise described and disclosed herein, comprising a plurality of submersible ammonia-sensing portions, wherein at least two of the ammonia sensing portions have different ammonia sensitivities. In certain implementations, the at least two ammonia sensing portions having different ammonia sensitivities each have a different sensitivity range selected from the ammonia sensitivity range group consisting of about 0.05 to about 0.5 ppm, about 0.05 to about 1.0 ppm, about 0.005 to about 0.1 ppm, about 0.005 ppm to about 0.05 ppm, and about 0.005 ppm to 0.05 ppm, about 0.005 ppm to about 0.01 ppm, or about 0.005 ppm to 0.01 ppm. In certain embodiments, the ammonia measuring device comprises at least three submersible ammonia-sensing portions each having a different ammonia sensitivity. In particular embodiments, the at least three ammonia sensing portions having different ammonia sensitivities each have a different sensitivity range selected from the ammonia sensitivity range group consisting of about 0.05 to about 0.5 ppm, about 0.05 to about 1.0 ppm, about 0.005 to about 0.1 ppm, about 0.005 ppm to about 0.05 ppm, about 0.005 ppm to 0.05 ppm, about 0.005 ppm to about 0.01 ppm, and 0.005 ppm to 0.01 ppm.

Yet additional embodiments provide a combination pH and ammonia measuring device as otherwise disclosed and described herein, further comprising a temperature sensing portion (e.g., a liquid cystal-based thermometer) to provide for readout of temperature.

Further aspects provide a combination pH and ammonia measuring device, comprising at least one main body member having face and side surfaces, the member comprising at least one ammonia sensing portion and at least one pH sensing portion, wherein at least one of the ammonia sensing and pH sensing portions is suitably configured and disposed to extend sufficiently horizontally around at least one of the side surfaces of the main body, or a portion thereof, of the main body member sensor so that a side view of at least one of the ammonia sensing and pH sensing portions by a user is operatively sufficient to provide at least one of ammonia and pH sensor input to the user. In particular embodiments, the main body member comprises a substantially rectangular or square planar plate having front and rear plate face surfaces defining a plate depth, and having side surfaces.

The invention claimed is:

1. A combination pH and ammonia measuring device for simultaneous, continuous measurement of solution pH and ammonia, the combination comprising:
   a submersible member, or a plurality of spatially proximate, coordinately-submersible members, suitable to be at least partially submersible in a solution;
   at least one submersible ammonia-sensing portion integral with or attached to the submersible member or to one or more of the proximate submersible members, the at least one ammonia-sensing portion having at least one stable detection means suitable to provide for a continuous visual indicator of solution ammonia concentration;
   at least one submersible pH-sensing portion integral with or attached to the submersible member or to one or more of the proximate submersible members, the at least one pH-sensing portion having at least one stable detection means suitable to provide for a continuous visual indicator of solution pH;
   a visual ammonia indicator comparison component, comparable with the at least one continuous visual indicator of the at least one ammonia-sensing portion to provide for standardized quantitative determination of solution ammonia concentration; and
   a visual pH indicator comparison component, comparable with the at least one continuous visual indicator of the at least one pH-sensing portion for standardized quantitative determination of solution pH, wherein the combination is suitable to provide for simultaneous, continuous measurement of solution pH and ammonia.

2. The combination pH and ammonia measuring device of claim 1, wherein the at least one continuous visual indicator of the at least one ammonia-sensing portion comprises at least one colorimetric dye indicator.

3. The combination pH and ammonia measuring device of claim 1, wherein the at least one continuous visual indicator of the at least one pH-sensing portion comprises at least one colorimetric dye indicator.

4. The combination pH and ammonia measuring device of claim 2, wherein the at least one visual ammonia indicator comparison component comprises at least one ammonia reference color indicator comparison chart integral with or attached to the submersible member or to the proximate coordinately-submersible members.

5. The combination pH and ammonia measuring device of claim 2, wherein the visual ammonia indicator comparison component comprises at least one ammonia reference color indicator comparison chart that is physically separate from, but moveable to a position spatially proximate to the at least one ammonia-sensing portion of the submersible member or the proximate submersible members to be comparable therewith.

6. The combination pH and ammonia measuring device of claim 4, wherein the at least one ammonia reference color indicator comparison chart comprises at least one color-gradient indicator comparison chart.

7. The combination pH and ammonia measuring device of claim 6, wherein the at least one color-gradient indicator comparison chart comprises at least one linear color-gradient chart, or circular or wheel color-gradient chart.

8. The combination pH and ammonia measuring device of claim 3, wherein the at least one visual pH indicator comparison component comprises at least one pH reference color indicator comparison chart integral with or attached to the submersible member or to the proximate submersible members.

9. The combination pH and ammonia measuring device of claim 3, wherein the visual pH indicator comparison means comprises at least one pH reference color indicator comparison chart that is physically separate from, but movable to a position spatially proximate to the at least one pH-sensing portion of the submersible member or to the proximate submersible members to be comparable therewith.

10. The combination pH and ammonia measuring device of claim 8, wherein the at least one pH reference color indicator comparison chart comprises at least one color-gradient indicator comparison chart.

11. The combination pH and ammonia measuring device of claim 10, wherein the at least one color-gradient indicator comparison chart comprises at least one linear color-gradient chart, or circular or wheel color-gradient chart.

12. The combination pH and ammonia measuring device of claim 1, wherein the at least one ammonia-sensing portion is suitable to detect ammonia in the range of about 0.05 to about 0.5 ppm, about 0.05 to about 1.0 ppm, or about 0.005 to about 0.1 ppm.

13. The combination pH and ammonia measuring device of claim 12, wherein the at least one ammonia-sensing portion is suitable to detect ammonia in the range of about 0.005 to about 0.1 ppm.

14. The combination pH and ammonia measuring device of claim 2, wherein the at least one ammonia-sensing portion comprises a bromophenol blue dye in a porous PTFE support.

15. The combination pH and ammonia measuring device of claim 1, further comprising relational means for quantitatively determining total ammonia ($NH_3$ plus $NH_4^+$), based on the at least one visual indicator of solution ammonia concentration and the at least one visual indicator of solution pH, in combination with the respective at least one quantitative ammonia and pH comparison components.

16. A combination pH and ammonia measuring device for simultaneous, continuous measurement of solution pH and ammonia, the combination comprising:
  an attachment base member;
  a submersible member, or a plurality of spatially proximate, coordinately-submersible members, reversibly attachable to the attachment base member, and suitable to be at least partially submersible in a solution;
  at least one submersible ammonia-sensing portion integral with or attached to the submersible member or to one or more of the proximate submersible members, the at least one ammonia-sensing portion having at least one stable detection means suitable to provide for a continuous visual indicator of solution ammonia concentration;
  at least one submersible pH-sensing portion integral with or attached to the submersible member or to one or more of the proximate submersible members, the at least one pH-sensing portion having at least one stable detection means suitable to provide for a continuous visual indicator of solution pH;
  a visual ammonia indicator comparison component, comparable with the at least one continuous visual indicator of the at least one ammonia-sensing portion to provide for standardized quantitative determination of solution ammonia concentration; and
  a visual pH indicator comparison component, comparable with the at least one continuous visual indicator of the at least one pH-sensing portion to provide for standardized quantitative determination of solution pH, wherein the combination is suitable to provide for simultaneous, continuous measurement of solution pH and ammonia.

17. The combination pH and ammonia measuring device of claim 16, wherein the at least one continuous visual indicator of the at least one ammonia-sensing portion comprises at least one colorimetric dye indicator.

18. The combination pH and ammonia measuring device of claim 16, wherein the at least one continuous visual indicator of the pH-sensing portion comprises at least one colorimetric dye indicator.

19. The combination pH and ammonia measuring device of claim 17, wherein the visual ammonia indicator comparison component comprises at least one ammonia reference color indicator comparison chart integral with or attached to the attachment base member.

20. The combination pH and ammonia measuring device of claim 17, wherein the visual ammonia indicator comparison component comprises at least one ammonia reference color indicator comparison chart that is physically separate from the attachment base member, but movable to a position spatially proximate to the at least one ammonia-sensing portion of the submersible member or the proximate submersible members to be comparable therewith.

21. The combination pH and ammonia measuring device of claim 19, wherein the at least one ammonia reference color indicator comparison chart comprises at least one color-gradient indicator comparison chart.

22. The combination pH and ammonia measuring device of claim 21, wherein the at least one color-gradient indicator comparison chart comprises at least one linear color-gradient chart, or circular or wheel color-gradient chart.

23. The combination pH and ammonia measuring device of claim 18, wherein the visual pH indicator comparison component comprises at least one pH reference color indicator comparison chart integral with or attached to the attachment base member.

24. The combination pH and ammonia measuring device of claim 18, wherein the visual pH indicator comparison component comprises at least one pH reference color indicator comparison chart that is physically separate from the attachment base member, but movable to a position spatially proximate to the at least one ammonia-sensing portion of the submersible member or the proximate submersible members, to be comparable therewith.

25. The combination pH and ammonia measuring device of claim 23, wherein the at least one pH reference color indicator comparison chart comprises at least one color-gradient indicator comparison chart.

26. The combination pH and ammonia measuring device of claim 25, wherein the at least one color-gradient indicator comparison chart comprises at least one linear color-gradient chart, or circular or wheel color-gradient chart.

27. The combination pH and ammonia measuring device of claim 16, wherein the at least one ammonia-sensing portion is suitable to detect ammonia in the range of about 0.05 to about 0.5 ppm, about 0.05 to about 1.0 ppm, or about 0.005 to about 0.1 ppm.

28. The combination pH and ammonia measuring device of claim 27, wherein the at least one ammonia-sensing portion is suitable to detect ammonia in the range of about 0.005 to about 0.1 ppm.

29. The combination pH and ammonia measuring device of claim 17, wherein the at least one ammonia-sensing portion comprises a bromophenol blue dye in a porous PTFE support.

30. The combination pH and ammonia measuring device of claim 16, wherein the attachment base member is at least partially submersible in a solution, and wherein the visual ammonia indicator comparison component and the visual pH indicator comparison component are integral with or attached to the attachment base member or to the submersible member or to at least one of the proximate submersible members.

31. The combination pH and ammonia measuring device of claim 16, further comprising relational means to quantitatively determine total ammonia ($NH_3$ plus $NH_4^+$), based on the at least one visual indicator of solution ammonia concentration and the at least one visual indicator of solution pH, in combination with the respective at least one quantitative ammonia and pH comparison components.

32. The combination pH and ammonia measuring device of any one of claims 1 and 16, wherein at least one of the at least one submersible ammonia-sensing portion or the at least one submersible pH-sensing portion further comprises an antimicrobial agent.

33. The combination pH and ammonia measuring device of claim 32, wherein the antimicrobial agent comprises at least one agent selected from the group consisting of silver, colloidal silver, silver dioxide, titanium dioxide, Triclosan, or thiabendazole-based antimicrobials, silane quaternary ammonium salts, and 3-(trimethoxysilyl)propyldimethyl octadecyl ammonium.

34. The combination pH and ammonia measuring device of claim 32, wherein the antimicrobial agent comprises a barrier material having pores small enough to preclude contact of the sensor by microbes, but large enough to allow for passage of water and ions therethrough.

35. The combination pH and ammonia measuring device of claim 32, wherein the barrier material comprises at least one porous membrane material selected from the group consisting of polyether sulfone, nylon, and polycarbonate.

36. An ammonia detection device, comprising porous matrix polytetrafluoroethylene (PTFE) having an ammonia-sensitive immobilized dye, the immobilized dye suitable to provide for a colorimetric determination of ammonia level, and wherein the detectible range of ammonia comprises a range of about 0.005 to about 0.1 ppm.

37. The ammonia detection device of claim 36, wherein the ammonia-sensitive immobilized dye is BPB dye.

38. The ammonia detection device of claim 36, wherein the porous matrix polytetrafluoroethylene (PTFE) comprises a composite supported microporous PTFE medium, comprising a PTFE microporous membrane having secured directly to at least one face thereof a PTFE web of microfibres.

39. The device of claim 36, wherein colorimetric determination of ammonia level is continuous and reversible within the detectible range.

40. The combination pH and ammonia measuring device of any one of claims 1 and 16, comprising a plurality of submersible ammonia-sensing portions, wherein at least two of the ammonia sensing portions have different ammonia sensitivities.

41. The combination pH and ammonia measuring device of claim 40, wherein the at least two ammonia sensing portions having different ammonia sensitivities each have a different sensitivity range selected from the ammonia sensitivity range group consisting of about 0.05 to about 0.5 ppm, about 0.05 to about 1.0 ppm, about 0.005 to about 0.1 ppm, about 0.005 ppm to about 0.05 ppm, and about 0.005 ppm to 0.05 ppm.

42. The combination pH and ammonia measuring device of claim 40, comprising at least three submersible ammonia-sensing portions each having a different ammonia sensitivity.

43. The combination pH and ammonia measuring device of claim 42, wherein the at least three ammonia sensing portions having different ammonia sensitivities each have a different sensitivity range selected from the ammonia sensitivity range group consisting of about 0.05 to about 0.5 ppm, about 0.05 to about 1.0 ppm, about 0.005 to about 0.1 ppm, about 0.005 ppm to about 0.05 ppm, and about 0.005 ppm to 0.05 ppm.

44. The combination pH and ammonia measuring device of any one of claims 1 and 16, further comprising a temperature sensing portion to provide for readout of temperature.

45. The combination pH and ammonia measuring device of any one of claims 1 and 16, wherein at least one of the ammonia sensing and pH sensing portions is suitably configured and disposed to extend sufficiently horizontally around one or more sides of the main body member so that a side view of at least one of the ammonia sensing and pH sensing portions by a user is operatively sufficient to provide for sensor input to the user.

46. A pH or ammonia measuring device, or a combination pH and ammonia measuring device, comprising at least one main body member having face and side surfaces, the member comprising at least one ammonia sensing portion and at least one pH sensing portion, wherein at least one of the ammonia sensing and pH sensing portions is suitably configured and disposed to extend sufficiently horizontally around at least one of the side surfaces, or a portion thereof, of the main body member sensor so that a side view of at least one of the ammonia sensing and pH sensing portions by a user is operatively sufficient to provide for at least one of ammonia and pH sensor input to the user.

47. The pH and ammonia measuring device of claim 46, wherein the main body member comprises a plate having front and rear plate face surfaces defining a plate depth, and having side surfaces.

48. A pH or ammonia measuring device, or a combination pH and ammonia measuring device, comprising at least one of a light-sensitive sensor dye and ink; and at least one light blocking element to reduce or preclude degrading or bleaching of the sensor dye or ink.

49. The combination pH and ammonia measuring device of any one of claims 1 and 16, comprising at least one light blocking element to reduce or preclude degrading or bleaching of the sensor dyes, or of the inks used to create the at least one comparative standard indicator component.

50. The combination pH and ammonia measuring device of claim 49, wherein the light blocking aspect comprises a light-absorbing or reflective shield or shroud operatively positionable to cover at least a portion of the sensor device.

* * * * *